US010525141B2

(12) United States Patent
Haag et al.

(10) Patent No.: US 10,525,141 B2
(45) Date of Patent: Jan. 7, 2020

(54) POLYGLYCEROL DERIVATIVE AND A METHOD FOR MANUFACTURING THE SAME

(71) Applicant: FREIE UNIVERSITÄT BERLIN, Berlin (DE)

(72) Inventors: Rainer Haag, Berlin (DE); Sabine Reimann, Berlin (DE); Jens Dernedde, Berlin (DE)

(73) Assignee: FREIE UNIVERSITÄT BERLIN, Berlin (DE)

( * ) Notice: Subject to any disclaimer, the term of this patent is extended or adjusted under 35 U.S.C. 154(b) by 0 days.

(21) Appl. No.: 15/566,717

(22) PCT Filed: Apr. 15, 2016

(86) PCT No.: PCT/EP2016/058393
§ 371 (c)(1),
(2) Date: Oct. 15, 2017

(87) PCT Pub. No.: WO2016/166317
PCT Pub. Date: Oct. 20, 2016

(65) Prior Publication Data
US 2018/0092982 A1   Apr. 5, 2018

(30) Foreign Application Priority Data
Apr. 15, 2015   (DE) .................. 10 2015 206 819

(51) Int. Cl.
*A61K 47/10* (2017.01)
*A61K 47/60* (2017.01)
*C08G 65/22* (2006.01)
*C08G 65/34* (2006.01)
*C08G 83/00* (2006.01)

(52) U.S. Cl.
CPC .............. *A61K 47/60* (2017.08); *A61K 47/10* (2013.01); *C08G 65/22* (2013.01); *C08G 65/34* (2013.01); *C08G 83/004* (2013.01)

(58) Field of Classification Search
CPC ........ A61K 47/60; A61K 47/10; C08G 65/22; C08G 65/34; C08G 83/004
See application file for complete search history.

(56) References Cited

U.S. PATENT DOCUMENTS

| 2011/0065896 | A1* | 3/2011 | Licha et al. |
| 2011/0117009 | A1 | 5/2011 | Kratz et al. |
| 2012/0328519 | A1 | 12/2012 | Haag et al. |
| 2013/0095035 | A1 | 4/2013 | Licha et al. |
| 2015/0011003 | A1 | 1/2015 | Kuriyama et al. |

FOREIGN PATENT DOCUMENTS

| DE | 10 2006 036326 A1 | 7/2008 |
| EP | 2832848 A1 | 4/2015 |
| WO | 2011095311 A1 | 8/2011 |
| WO | 2012/156094 A1 | 11/2012 |

OTHER PUBLICATIONS

H. Türk et al., Dec. 6, 2003, Dendritic Polyglycerol Sulfates as New Heparin Analogues and Potent Inhibitors of the Complement System, Bioconjugate Chemistry, 15, 162-167.
J. Demedde, Nov. 16, 2010, Dendritic polyglycerol sulfates as multivalent inhibitors of inflammation, Proceedings of the National Academy of Sciences, 107, 19679-19684.
K. Oishi et al., Jun. 27, 2014, A Crucial Role of L-Selectin in C Protein-Induced Experimental Polymyositis in Mice, Arthritis Rheumatology, 66, 1864-1871.
Bryant, et al., "Synthesis and Characterization of Photopolymerized Multifunctional Hydrogels: Water-Soluble Poly (Vinyl Alcohol) and Chondroitin Sulfate Macromers for Chondrocyte Encapsulation," Macromolecules, vol. 37, No. 18, 2004, pp. 6726-6733.
Capila, I, and Linhardt, RJ., "Heparin-Protein Interactions," Angewandte Chemie International Edition, vol. 41, No. 3, 2002, pp. 390-412.
Casu et al., "Heparin-derived heparan sulfate mimics that modulate inflammation and cancer," Matrix Biology, vol. 29, No. 6, 2010, pp. 442-452.
Du Clos, T.W. and Mold, C., "Complement and complement deficiencies," in Clinical Immunology (Third Edition) (Ed.: R R. R. A. F. T.S. W. S. J. F. M. Weyand), Mosby, Edinburgh, 2008, pp. 305-325.
Enders et al., "Inhibition of L-selectin binding by polyacrylamide-based conjugates under defined flow conditions," Biochimica et Biophysica Acta (BBA)—General Subjects, vol. 1770, No. 10, 2007, pp. 1441-1449.
Gröger et al., "Synthesis and Biological Evaluation of Radio and Dye Labeled Amino Functionalized Dendritic Polyglycerol Sulfates as Multivalent Anti-Inflammatory Compounds," Bioconjugate Chemistry, vol. 24, No. 9, 2013, pp. 1507-1514.
Holzhausen et al., "Tissue and cellular localization of nanoparticles using 35S labeling and light microscopic autoradiography," Nanomedicine:Nanotechnology, Biology and Medicine, vol. 9, No. 4, 2013, pp. 465-468.
Hu et al., "Biodegradable Hyperbranched Polyglycerol with Ester Linkages for Drug Delivery," Biomacromolecules, vol. 13, No. 11, 2012, pp. 3552-3561.
Imai, T., "Human Carboxylesterase Isozymes: Catalytic Properties and Rational Drug Design," Drug Metabolism and Pharmacokinetics, vol. 21, No. 3, 2006, pp. 173-185.

(Continued)

*Primary Examiner* — Alma Pipic
(74) *Attorney, Agent, or Firm* — Maschoff Brennan

(57) ABSTRACT

It is provided a polyglycerol derivative, comprising a dendritic polyglycerol backbone and at least one substituent in the nature of a covalently bound negatively charged group chosen from the group consisting of sulfates, sulfonates, phosphates, phosphonates, bisphosphonates, carboxylates and combinations thereof. The substituent is bound to the polyglycerol backbone via a linker, the linker being chosen from the group consisting of moieties being or comprising a carbamate group, an ester group, an orthoester group, an amide group, a disulfide bridge group, an acetal group, an imine group and combinations thereof.

9 Claims, 8 Drawing Sheets

(56) References Cited

OTHER PUBLICATIONS

Kaila, N., and Thomas, B.E., "Selectin inhibitors," Expert Opinion on Therapeutic Patents, vol. 13, No. 3, 2003, pp. 305-317.
Kelly et al., "Modulating leukocyte recruitment in inflammation," Journal of Allergy and Clinical Immunology, vol. 120, No. 1, 2007, pp. 3-10.
Kirschfink, M., "Controlling the complement system in inflammation," Immunopharmacology, vol. 38, No. 1-2, 1997, pp. 51-62.
Lefer, D.J., "Pharmacology of Selectin Inhibitors in Ischemia/Repeifusion States," Annual Review of Pharmacology & Toxicology, vol. 40, 2000, pp. 283-294.
Ley et al., "Getting to the site of inflammation: the leukocyte adhesion cascade updated," Nature Reviews Immunology, vol. 7, No. 9, 2007, pp. 678-689.
Ley, K. "The role of selectins in inflammation and disease," Trends in Molecular Medicine, vol. 9, No. 6, 2003, pp. 263-268.
Licha et al., "Fluorescence Imaging with Multifunctional Polyglycerol Sulfates: Novel Polymeric near-IR Probes Targeting Inflammation," Bioconjugate Chemistry, vol. 22, No. 12, 2011, pp. 2453-2460.
McEver, R.P., and Zhu, C., "Rolling Cell Adhesion," Annual Review of Cell and Developmental Biology, vol. 26, 2010, pp. 363-396.
Medzhitov, R., "Origin and physiological roles of inflammation," Nature, vol. 454, 2008, pp. 428-435.
Nel et al., "Understanding biophysicochemical interactions at the nano-bio interface," Nat. Mater., vol. 8, No. 7, 2009, pp. 543-557.
Park et al., "Anti-inflammatory effects of fucoidan through inhibition of NF-κB, MAPK and Akt activation in lipopolysaccharide-induced BV2 microglia cells," Food and Chemical Toxicology, vol. 49, No. 8, 2011, pp. 1745-1752.
Pickaert et al., "A Convenient Protocol for the Synthesis of Ligands from a 4-Methyl-3,5-diacylaminophenyl Platform," The Journal of Organic Chemistry, vol. 69, No. 16, 2004, pp. 5335-5341.
Pomerantseva et al., "Degradation behavior of poly(glycerol sebacate)," Journal of Biomedical Materials Research Part A, vol. 91, No. 4, 2009, pp. 1038-1047.
Shenoi et al., "Biodegradable polyglycerols with randomly distributed ketal groups as multi-functional drug delivery systems," Biomaterials, vol. 34, No. 25, 2013, pp. 6068-6081.
Shenoi et al., "Synthesis, Characterization, and Biocompatibility of Biodegradable Hyperbranched Polyglycerols from Acid-Cleavable Ketal Group Functionalized Initiators," Biomacromolecules, vol. 13, No. 10, 2012, pp. 3018-3030.
Son et al. "Redox-Degradable Biocompatible Hyperbranched Polyglycerols: Synthesis, Copolymerization Kinetics, Degradation, and Biocompatibility," Macromolecules, vol. 48, No. 3, 2015, pp. 600-609.
Sunder et al., "Controlled Synthesis of Hyperbranched Polyglycerols by Ring-Opening Multibranching Polymerization," Macromolecules, vol. 32, No. 13, 1999, pp. 4240-4246.
Tonhauser et al., "Branched Acid-Degradable, Biocompatible Polyether Copolymers via Anionic Ring-Opening Polymerization Using an Epoxide Inimer," ACS Macro Letters, vol. 1, No. 9, 2012, pp. 1094-1097.
Volpi, N., "Anti-inflammatory activity of chondroitin sulphate: new functions from an old natural macromolecule," Inflammopharmacol, vol. 19, No. 6, 2011, pp. 299-306.
Wang et al., "Heparin's anti-inflammatory effects require glucosamine 6-O-sulfation and are mediated by blockade of L- and P-selectins," The Journal of Clinical Investigation, vol. 110, No. 1, 2002, pp. 127-136.
Warkentin, T.E., and Greinacher, A., "Heparin-Induced Thrombocytopenia and Cardiac Surgery," The Annals of Thoracic Surgery, vol. 76, No. 6, 2003, pp. 2121-2131.
Weinhart et al., "Synthesis of Dendritic Polyglycerol Anions and Their Efficiency Toward L-Selectin Inhibition," Biomacromolecules, vol. 12, No. 7, 2011, pp. 2502-2511.
Weinhart et al., "The Role of Dimension in Multivalent Binding Events: Structure-Activity Relationship of Dendritic Polyglycerol Sulfate Binding to L-Selectin in Correlation with Size and Surface Charge Density," Macromolecular Bioscience, vol. 11, No. 8, 2011, pp. 1088-1098.
Weiss, U, "Inflammation," Nature, vol. 454, No. 7203, 2008, p. 427.
White et al., "Effect of the carboxylesterase inhibitor bis-(4-nitrophenyl)phosphate in vivo on aspirin hydrolase and carboxylesterase activities at first-pass sites of metabolism in the guinea pig," Biochemical Pharmacology, vol. 36, No. 16, 1987, pp. 2687-2688.
Zhang, H., and Grinstaff, M.W., "Synthesis of Atactic and Isotactic Poly(1,2-glycerol carbonate)s: Degradable Polymers for Biomedical and Pharmaceutical Applications," Journal of the American Chemical Society, vol. 135, No. 18, 2013, pp. 6806-6809.
Tuerk H et al. "Dendritic Polyglycerol Sulfates as new Heparin Analogues and Potent Inhibitors of the Complement System." Bioconjugate Chemistry, ACS, Washington, DC, US, vol. 15, No. 1, Jun. 12, 2003.
Sabine Reimann et al. "Shell Cleavable Dendritic Polyglycerol Sulfates Show High Anti-Inflammatory Properties by Inhibiting L-Selection Binding and Complement Activation" Advanced Healthcare Materials, vol. 4, No. 4, pp. 2154-2162, Aug. 11, 2015.
Ana Sousa-Herves et al. "Dendritic Polyglycerol Sulfate as a Novel Platorm for Paclitaxel Delivery: Pitfalls of Ester Linkage" Nanoscale, vol. 7, No. 9, pp. 3923-3932, Jan. 1, 2015.
Shyam Rele et al. "Dendrimer-like PEO GlycopolymersExhibit Ana-Inflammatory Properties." Journal of the American Chemical Society, American Chemical Society, US, vol. 127, Jan. 1, 2005.

* cited by examiner

POLYGLYCEROL DERIVATIVE AND A METHOD FOR MANUFACTURING THE SAME

CROSS-REFERENCE TO A RELATED APPLICATION

This application is a National Phase Patent Application of International Patent Application Number PCT/EP2016/058393, filed on Apr. 15, 2016, which claims priority of German Patent Application Number 10 2015 206 819.6, filed on Apr. 15, 2015.

BACKGROUND

The instant invention relates to a polyglycerol derivative, to a medicament comprising such a polyglycerol derivative and to a method of manufacturing such a polyglycerol derivative.

As a part of the innate immune response to harmful stimuli such as physical injury, toxins, irritants or microbial infections, the acute inflammatory response triggers the removal of pathogens and subsequent dampening of inflammation is necessary to initiate the healing process. During this immune response increased leukocyte recruitment out of blood vessels into inflamed tissue is initiated which proceeds in a cascade-like fashion including the initial leukocyte tethering, subsequent rolling, firm adhesion to the endothelium, and subsequent transmigration into the subendothelial matrix.

The complex mechanism of leukocyte extravasation is mediated by cell adhesion molecules (CAMs) such as selectins and integrins, as well as chemokines and their respective ligands. For instance, the initial capture of leukocytes and subsequent rolling on the endothelium is initiated by the interaction of L-, P-, and E-selectin with their corresponding ligands consisting of fucosylated and sialylated glycoproteins.

Whereas acute inflammation describes a time limited and required process for healing, chronic inflammation is a persistent and unbalanced over reaction of the immune system, in which active inflammation and tissue damage, caused by prolonged excessive extravasation of leukocytes, are ongoing. Due to their essential role in leukocyte recruitment, different natural selectin inhibitors such as heparan sulfate, fucoidan and chondroitin sulfate have been investigated during the last decades for the treatment of inflammatory related diseases. However, the permanent suppression of the selectin-mediated immune response is certainly not the aim for a long term therapy, but is indeed useful for short-term treatments and diagnostic applications.

Another essential part within the inflammatory process is the activation of the complement system which can be achieved by the classical, alternative, and lectin pathway. Involving around 30 plasma proteins, the complement is responsible for opsonization of microorganisms for phagocytosis, recruitment of leukocytes and the lysis of pathogens.

Until today, heparin is the standard anticoagulant after surgery, but also provides high anti-inflammatory properties as found in an enzyme-linked immunosorbent assay (ELISA) investigating the binding affinity to L- and P-selectin and in an oxazolone induced allergic contact dermatitis mice model. Nevertheless, intravenous administration of heparin might lead to severe problems such as heparin-induced thrombocytopenia (HIT), prolonged bleeding, and the risk to acquire infections due to contaminated samples. These circumstances limit the usage of heparin as an anti-inflammatory compound.

Initially reported in 2004 by Turk et al. as a new synthetic heparin analog based on a dendritic polyglycerol (dPG) scaffold, dendritic polyglycerol sulfate (dPGS) was found to have an up to 24 times higher anti-inflammatory activity in vitro and only up to 34% anticoagulant activity compared to unfractionated heparin (UFH) [1]. Moreover, in a competitive, concentration dependent surface plasmon resonance (SPR)-based binding assay, a strong affinity of dPGS to L- and P-selectin was confirmed, with $IC_{50}$ values up to the picomolar range, with respect to size and surface charge [2].

Screening of different dPG based anions, including phosphate, phosphonate, bisphosphonate, carboxylate, sulfonate, and sulfate, dPGS was identified as the most potent polyanion regarding L- and P-selectin binding [3]. The anti-inflammatory potential of dPGS was also demonstrated in vivo by a dose dependent reduction of ear swelling after administration in an acute allergic contact dermatitis model [4]. Effective shielding of leukocytes was also found in an experimental model of polymyositis, where reduced tissue destruction was observed [5]. Further, due to its high affinity to inflamed tissue, dPGS conjugates were successfully applied in the past as diagnostics in a collagen induced arthritis rat model, with cyanine near-IR dyes as the fluorescent read out [6].

Despite this enormous potential as a drug candidate, recent in vivo studies with radiolabeled dPGS, with a hydrodynamic diameter below 6 nm, revealed undesired biodistribution properties in mice [7]. Accumulation of dPGS in liver and spleen was observed even 21 days after intravenous administration. The unexpected biodistribution of dPGS is probably caused by ionic interactions of the polysulfate with serum proteins which might lead to the formation of aggregates and consequently to an increased hydrodynamic diameter, resulting in the recognition of the particles by the reticuloendothelial system (RES) [7, 8].

US 2011/0117009 A1 discloses a drug polymer conjugate comprising a pharmaceutically active compound and a dendritic polyglycerol. The conjugates are very complex molecules.

DE 10 2006 036 326 A1 discloses dendritic polyglycerol sulfates and dendritic polyglycerol sulfonates and their use for treating inflammatory diseases.

SUMMARY

It is an object of the present invention to provide novel compounds that overcome the disadvantages of prior art. In particular, novel compounds being suited as anti-inflammatory compounds having a better biocompatibility and better biodistribution properties than dPGS shall be provided.

This object is achieved by a polyglycerol derivative having features as described herein. Such a polyglycerol derivative comprises a dendritic polyglycerol backbone and at least one substituent in the nature of a covalently bound negatively charged group chosen from the group consisting of sulfates, sulfonates, phosphates, phosphonates, bisphosphonates, carboxylates and combinations thereof. According to the present invention, the polyglycerol derivative is characterized in that the substituent is bound to the polyglycerol backbone via a linker. This linker is designed and arranged to be cleaved under adjustable conditions. In order to achieve this aim, the linker is chosen from the group consisting of moieties being or comprising a carbamate group, an ester group, an orthoester group, an amide group, a disulfide bridge group, an acetal group, an imine group and combinations thereof.

In an embodiment, relatively stable functionalities are comprised within the linker to allow modification of the linker molecules also under harsh conditions without cleaving or degrading the linker molecules. To give an example, if the linker comprises an ester group, a carbamate group and/or an amide group, it is possible to sulfate, sulfonate, phosphate, phosphonate, bisphosphonate or carboxylate the linker bound to the polyglycerol backbone without cleaving the linker molecule. Thereby, it is in particular possible to sulfate the linker molecules already bound to the polyglycerol backbone.

In an embodiment, the substituent is sulfate. As outlined above, dendritic polyglycerol sulfates (dPGS) are particularly suited as anti-inflammatory compounds. Surprisingly, it could be shown that dPGS comprising a linker molecule as specified above even show a higher biological activity then "classic" dPGS without such linker molecules. By introducing a linker molecule as specified above, a core-shell structure of dPGS is achieved (the core being the backbone of the polyglycerol and the shell being the linker and sulfate groups), wherein the shell is cleavable from the core. This is achieved by the cleavable linker molecule. An according dPGS can also be denoted as shell cleavable dPGS. Similarly, polyglycerol compounds bearing other negatively charged group can be denoted as shell cleavable anionic dPG.

In an embodiment, a degree of substitution of the backbone is between 10 and 100% (including the upper and lower limit). In an embodiment, the degree of substitution of the backbone is between 15% and 95%, in particular between 20% and 90%, in particular between 25% and 85%, in particular between 30% and 80%, in particular between 35% and 75%, in particular between 40% and 70%, in particular between 45% and 65%, in particular between 50% and 60%, in particular between 55% and 58%, (in each case including the upper and lower limits). A very well suited range of substitution is between 70% and 100% (including the upper and lower limit).

The degree of substitution, in particular the degree of sulfation, can be adjusted by adjusting the experimental conditions under which the substitution takes place.

The dendritic backbone of the polyglycerol compound can also be denoted as hyperbranched backbone. Thus, the polyglycerol compound can also be denoted as hyperbranched polyglycerol (hPG). In case of sulfate groups as substituents, the polyglycerol can be denoted as hyperbranched polyglycerol sulfate (hPGS). Hyperbranched polyglycerol sulfates (hPGS) express little or no anticoagulant effect.

In an embodiment, the linker is or comprises at least an ester group or only an ester group. On the one hand, such an ester group can be cleaved comparatively easily so that the shell can be cleaved from the polyglycerol backbone or core. In doing so, the biodegradability of the polyglycerol compounds is significantly increased since the polyglycerol backbone and the shell bearing negatively charged groups can be degraded separately from each other. Thereby, an accumulation of the polyglycerol compounds in the spleen, kidney or liver is circumvented so that the plasma half-life is significantly reduced with respect to polyglycerol compounds bearing negatively charged groups on a non-cleavable shell. On the other hand, such an ester group is comparatively stable so that it can survive also harsh conditions which might be necessary to introduce a negatively charged group onto the linker molecule if it is already bound to the polyglycerol backbone.

In an embodiment, the linker is or comprises an ester group and a carbamate group. In another embodiment, the linker is or comprises an ester group and an amide group. In another embodiment, the linker is or comprises a carbamate group and an amide group.

In an embodiment, the linker is a substituted or non-substituted hydrocarbon residue that comprises a carbamate group, an ester group, an orthoester group, an amide group, a disulfide bridge group, an acetal group, an imine group and combinations thereof, that is optionally interrupted by at least one additional N, O and/or S atom. Thereby, it can comprise, in an embodiment, 1 to 10 carbon atoms.

In an embodiment, the hydrocarbon residue is a substituted or non-substituted $C_1$-$C_{10}$ alkyl that is optionally interrupted by at least one N, O and/or S atom and that comprises a carbamate group, an ester group, an orthoester group, an amide group, a disulfide bridge group, an acetal group, an imine group and combinations thereof.

In an embodiment, a plurality of hydroxyl groups of the polyglycerol backbone are substituted by at least one of the following substituents R:

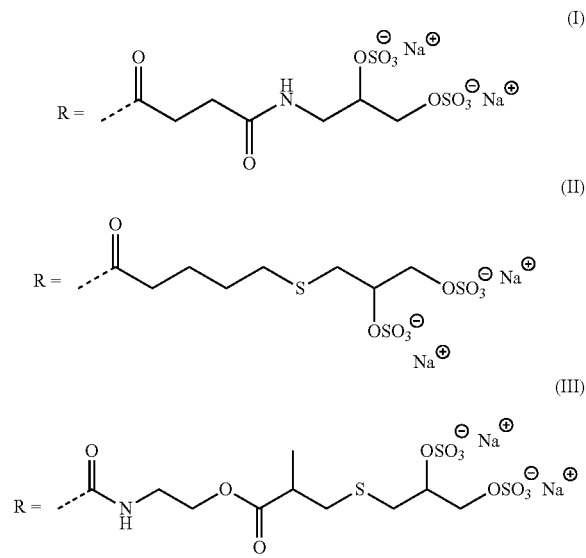

Thereby, the counter-ion which is indicated to be $Na^+$ can also be different from $Na^+$. To give an example, all alkali metal ions are suited as counter ions. The linker of formula (I) is bound to the polyglycerol backbone via an ester group (one oxygen atom of the ester group is provided by the polyglycerol backbone; it is not indicated in the above-given formula; the linkage to the polyglycerol backbone is achieved via an OR bond). It additionally comprises an amide group. The linker of formula (II) is bound to the polyglycerol backbone also via an ester group. The linker of formula (III) is bound to the polyglycerol backbone via a carbamate group. It additionally comprises an ester group. All linker carry sulfate groups as negatively charged groups.

The polyglycerol derivative as described above has a very good anti-inflammatory activity. This will be shown in detail with respect to exemplary embodiments. Due to this activity, the use of such a polyglycerol derivative as drug is also claimed.

In an embodiment, the drug is a drug for inhibiting the complement system of an organism and/or for inhibiting L-selectin binding to its natural receptor. By such an inhibition, an anti-inflammatory effect is achieved. Thus, in an embodiment, the polyglycerol derivative is used as drug for treating an inflammatory disease.

In another embodiment, the polyglycerol derivative is used for targeting inflammatory tissue in vivo. It is possible to couple the polyglycerol derivative with a detectable probe so as to use the construct of polyglycerol derivative and probe for diagnosing inflammatory diseases, in particular chronic inflammatory diseases such as rheumatoid arthritis or psoriasis or acute inflammatory processes such as those occurring after an organ transplant. Suited detectable probes are fluorescence probes, contrast agents, magnetic agents etc.

In an embodiment, the invention relates to a drug comprising a polyglycerol derivative according to the preceding explanations as active ingredient. However, the polyglycerol derivative cannot be used only as active ingredient, but also as a carrier molecule for transporting other molecules to a desired site of action (such as inflammatory tissue). Therefore, the invention relates in an embodiment also to a drug comprising both a polyglycerol derivative and additionally a pharmaceutically active substance. Thereby, the polyglycerol derivative mainly acts as carrier for the pharmaceutically active substance.

The invention also relates to a method for manufacturing a polyglycerol derivative according to the preceding explanations. This method is characterized by the following steps:
a) converting a polyglycerol having a dendritic polyglycerol backbone with a substituted or non-substituted $C_1$-$C_{10}$ alkyl that is optionally interrupted by at least one N, O and/or S atom or with a substituted or non-substituted $C_1$-$C_{10}$ alkenyl that is optionally interrupted by at least one N, O and/or S atom,
b) converting the product obtained in step a) with a substituted or non-substituted $C_1$-$C_{10}$ alkylol carrying at least one hydroxyl group, wherein the hydrocarbon chain of the alkylol is optionally interrupted by at least one N, O and/or S atom,
c) converting the product in step b) with a compound being able to transfer a negatively charged group onto the at least one hydroxyl group of the $C_1$-$C_{10}$ alkyl used in step b).

In an embodiment, the $C_1$-$C_{10}$ alkyl or $C_1$-$C_{10}$ alkenyl of step a) is chosen from the group consisting of $C_1$-$C_{10}$ carbonic acid anhydrides, $C_1$-$C_{10}$ alkenoyl halogenides and isocyanato-alkyl methacrylates. Succinic anhydride is a particularly well suited carbonic acid anhydride. A $C_1$-$C_{10}$ alkenoyl chloride is a particularly well suited $C_1$-$C_{10}$ alkenoyl halogenide. To give specific examples, propenoyl chloride and pentenoyl chloride are well suited $C_1$-$C_{10}$ alkenoyl chlorides. 2-isocyanato-ethyl methacrylate is a particularly well suited isocyanato-alkyl methacrylate.

Suited reaction conditions for the conversion step a) are a temperature between 0° C. to 30° C., in particular between 5° C. and 25° C. (also denoted as room temperature, rt), in particular between 10° C. and 15° C., and reaction times of 12 to 72 hours, in particular 24 to 60 hours, in particular 36 to 48 hours, if a $C_1$-$C_{10}$ carbonic acid anhydride is used as conversion reagent. Thereby it is suited to solve the reaction partners in a non-polar solvent such as pyridine.

Suited reaction conditions for the conversion step a) are a temperature between 0° C. to 30° C., in particular between 5° C. and 25° C., in particular between 10° C. and 15° C., and reaction times of 10 minutes to 24 hours, in particular 30 minutes to 12 hours, in particular 1 hour to 10 hours, in particular 2 hours to 5 hours, if a $C_1$-$C_{10}$ alkenoyl halogenide is used as conversion reagent. Thereby it is suited to solve the reaction partners in a non-polar solvent such as triethylamine ($NEt_3$).

Suited reaction conditions for the conversion step a) are a temperature between 20° C. to 80° C., in particular between 30° C. and 70° C., in particular between 40° C. and 65° C., in particular between 50° C. and 60° C., and reaction times of 10 minutes to 24 hours, in particular 30 minutes to 12 hours, in particular 1 hour to 10 hours, in particular 2 hours to 5 hours, if an isocyanato-alkyl methacrylate is used as conversion reagent. Thereby it is suited to solve the reaction partners in a polar solvent such as dimethylformamide (DMF).

In an embodiment, the $C_1$-$C_{10}$ alkylol of step b) is glycerol, a thioglycerol or an aminoglycerol.

Suited reaction conditions for the conversion step b) are a temperature between 0° C. to 30° C., in particular between 5° C. and 25° C., in particular between 10° C. and 15° C., and reaction times of 10 minutes to 24 hours, in particular 30 minutes to 12 hours, in particular 1 hour to 10 hours, in particular 2 hours to 5 hours, if amino glycerol is used as conversion reagent. Thereby it is suited to solve the reaction partners in a polar solvent such as water and/or to add a catalyst such as 4-(dimethylamino)-pyridine (DMAP) and/or to add an activating agent such as 1-ethyl-3-(3-dimethylaminopropyl)carbodiimide (EDC) or its hydrochloride EDC.HCl.

Suited reaction conditions for the conversion step b) are a temperature between 0° C. to 30° C., in particular between 5° C. and 25° C., in particular between 10° C. and 15° C., and reaction times of 10 minutes to 24 hours, in particular 30 minutes to 12 hours, in particular 1 hour to 10 hours, in particular 2 hours to 5 hours, if thioglycerol is used as conversion reagent. Thereby it is suited to solve the reaction partners in a polar solvent such as chloroform ($CHCl_3$) or DMF and/or to add a photoinitiator such as 2,2-dimethoxy-2-phenylacetophenone (DMPA) and apply UV light onto the reagents.

Suited reaction conditions for the conversion step c) are a temperature between 20° C. to 80° C., in particular between 30° C. and 70° C., in particular between 40° C. and 65° C., in particular between 50° C. and 60° C., and reaction times of 10 minutes to 24 hours, in particular 30 minutes to 12 hours, in particular 1 hour to 10 hours, in particular 2 hours to 5 hours. Thereby it is suited to solve the reaction partners in a polar solvent such as DMF.

In an embodiment, the compound being able to transfer a negatively charged group onto the at least one hydroxyl group of the $C_1$-$C_{10}$ alkyl used in step b) is a sulfation reagent. A suited sulfation reagent is sulfur trioxide pyridine ($SO_3$.Py).

All embodiments explained in connection to the claimed polyglycerol derivative can also be applied to the described medicament, the described uses and the described manufacturing process, and vice versa.

BRIEF DESCRIPTION OF THE DRAWINGS

Further aspects and details of the invention will be explained with respect to figures and exemplary embodiments.

FIG. 2B).

FIG. 2B).

FIG. 2B).

DETAILED DESCRIPTION

Figure 1A:
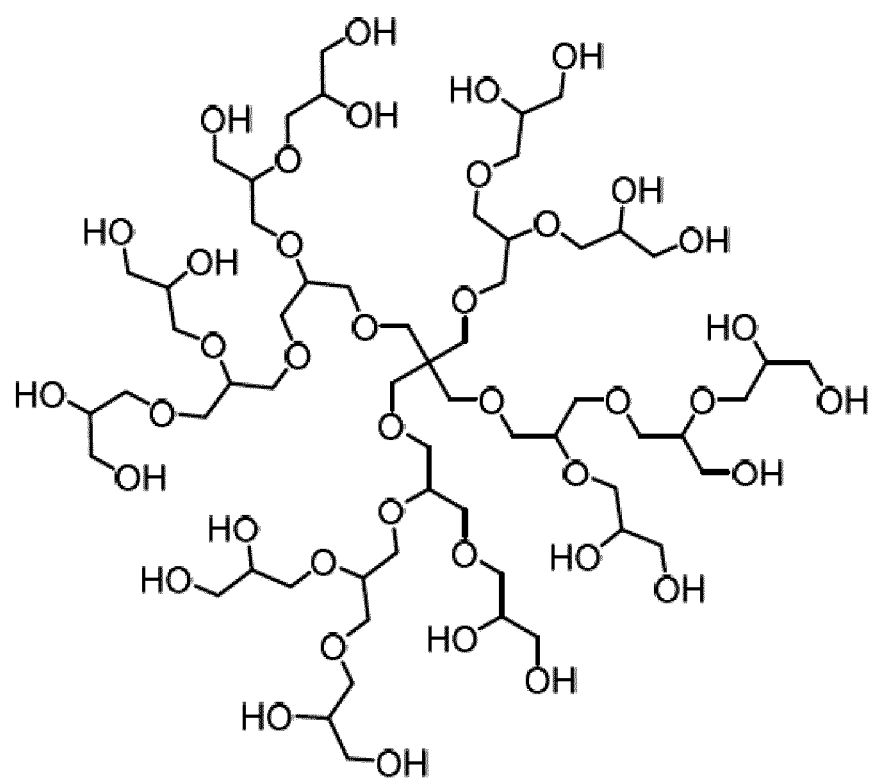
FIG. 1A shows the chemical structure of the polyglycerol backbone of an exemplary dendritic polyglycerol compound.

FIG. 1A is a schematic depiction of the polyglycerol backbone of an exemplary (idealized) dendritic polyglycerol (dPG). Such dPG can be used as starting point for preparing polyglycerol compounds.

Figure 1B:
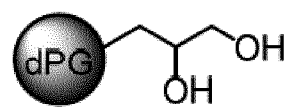
FIG. 1B shows a second possibility to depict the chemical structure of the polyglycerol of FIG. 1A.

FIG. 1B shows an abbreviated possibility to depict the polyglycerol structure of FIG. 1A. For sake of simplification only, the abbreviated depiction of FIG. 1B shows only two hydroxyl groups, although the polyglycerol bears significantly more hydroxyl groups (cf. FIG. 1A).

Figure 2A:
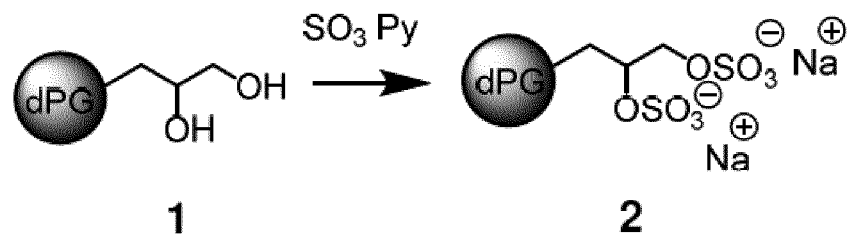
FIG. 2A shows a reaction scheme of the reaction of a polyglycerol to a polyglycerol sulfate according to prior art.

FIG. 2A shows the reaction scheme of sulfation of dendritic polyglycerol (dPG) 1 to dendritic polyglycerol sulfate (dPGS) 2. dPGS can also be denoted as stable polyglycerol sulfate. The sulfation was carried out by sulfur trioxide pyridine ($SO_3.Py$) as sulfation agent. This reaction is well known from prior art.

Figure 2B:
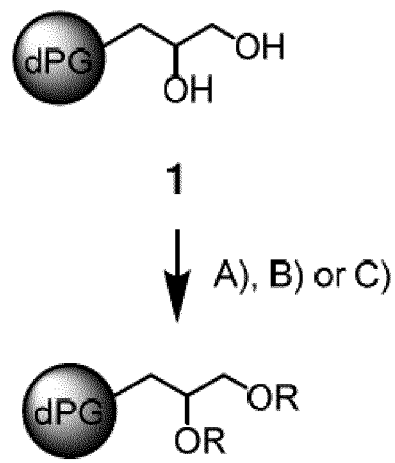
FIG. 2B shows the general reaction scheme of the reaction of polyglycerol to a substituted polyglycerol derivative.

FIG. 2B shows the reaction scheme of an exemplary embodiment for producing polyglycerol compounds that bear a linker are which differs from substitutes known from prior art. This reaction can be carried out, e.g., in 3 different ways A), B), C) that will be explained in more detail with respect to FIGS. 4A to 4C. The reaction products can be denoted as biodegradable dPGS.

Figure 3A:
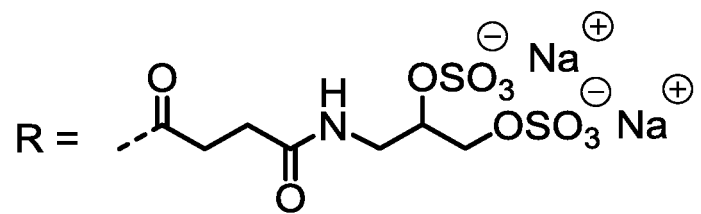
FIG. 3A shows a first residue R that can be used as substituent for substituting polyglycerol (cf.

FIG. 3A shows a residue R that can be the substituent of the polyglycerol compound produced according to the reaction scheme of FIG. 2B, wherein the resulting polyglycerol compound can be denoted as dPG-amidoglyceryl succinyl sulfate (dPG-ASuS).

Figure 3B:
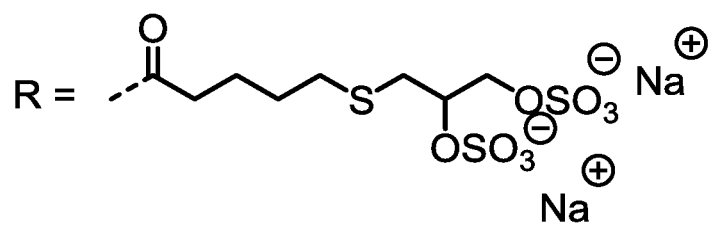
FIG. 3B shows a second residue R that can be used as substituent for substituting polyglycerol (cf.

FIG. 3B shows a residue R that can be the substituent of the polyglycerol compound produced according to the reaction scheme of FIG. 2B, wherein the resulting polyglycerol compound can be denoted as dPG-thioglyceryl pentanoatyl sulfate (dPG-TPS).

Figure 3C:
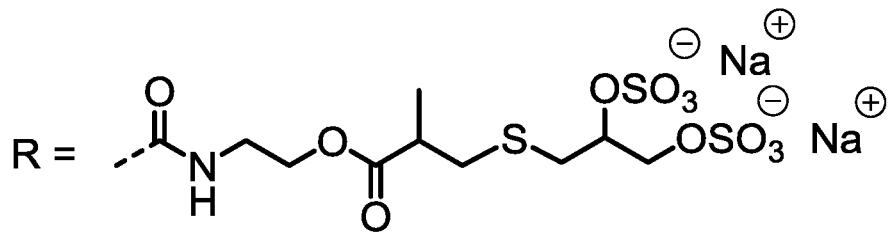
FIG. 3C shows a third residue R that can be used as substituent for substituting polyglycerol (cf.

FIG. 3C shows a residue R that can be the substituent of the polyglycerol compound produced according to the reaction scheme of FIG. 2B, wherein the resulting polyglycerol compound can be denoted as dPG-thioglyceryl methylpropanoatyl sulfate (dPG-TMPS).

FIGS. 4A to 8D will now be explained in more detail referring to exemplary embodiments.

Example: Synthesis and Characterization of Degradable Dendritic Polysulfates

With its multiple hydroxyl groups, dendritic polyglycerol (dPG) allows a versatile derivatization and the introduction of different functional groups. By implementation of cleavable linkers and subsequent sulfation, shell degradable compounds with a high anti-inflammatory activity could be developed, which lead to neutral dPG and multiple sulfated linkers of low molecular weight after full cleavage. To develop compounds with different degradation patterns, linkers varying in hydrophobicity, length and flexibility with hydrolytically or enzymatically cleavable groups were introduced to the dPG-backbone and investigated. Since the molecular weight of the polymer and the number of sulfate groups have a significant influence on the L-selectin binding [2] and hence anti-inflammatory activity, three biodegradable compounds with comparable molecular weights and numbers of sulfate groups were synthesized (cf. FIG. 2B in connection to FIGS. 3A, 3B and 3B; the individual reaction schemes are depicted in FIGS. 4A, 4B and 4C).

Figure 4A:
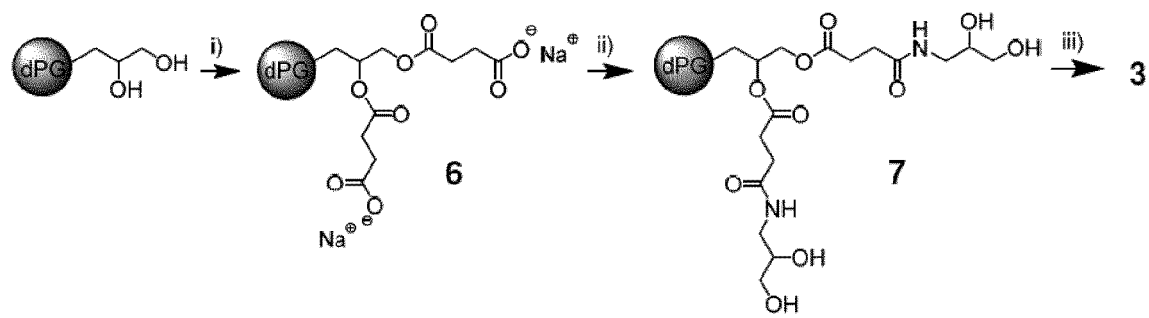
FIG. 4A shows a reaction scheme for the reaction of polyglycerol to a polyglycerol derivative bearing residue R of FIG. 3A.
Figure 4B:
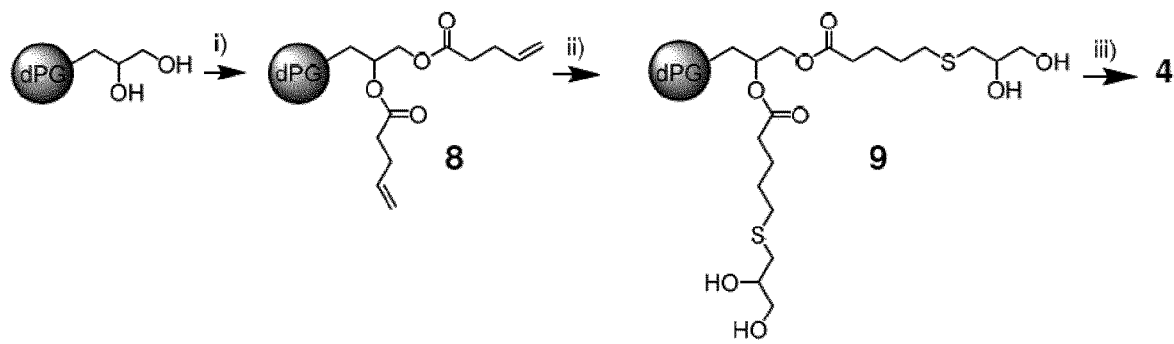
FIG. 4B shows a reaction scheme for the reaction of polyglycerol to a polyglycerol derivative bearing residue R of FIG. 3B.
Figure 4C:
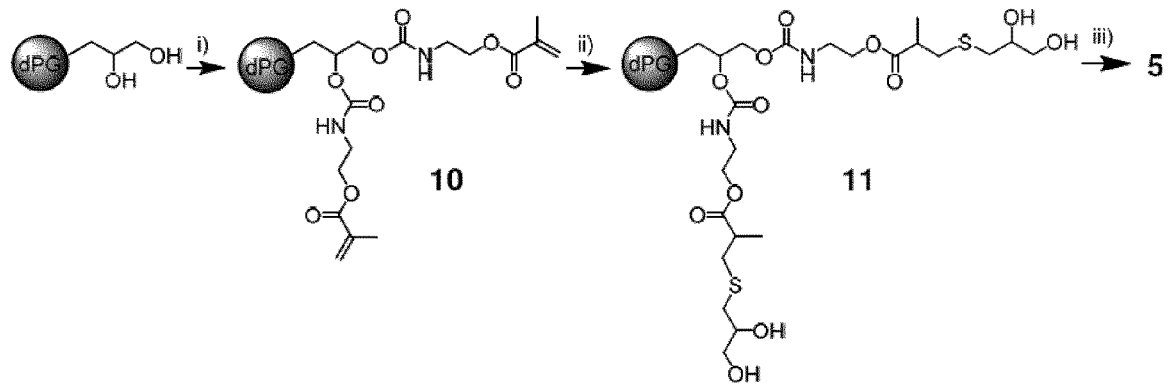
FIG. 4C shows a reaction scheme for the reaction of polyglycerol to a polyglycerol derivative bearing residue R of FIG. 3C.

Dendritic polyglycerol as the core scaffold was synthesized with a molecular weight of 5,100 g mol$^{-1}$, low PDI (1.6) and degree of branching of 60% via a controlled living anionic ring-opening multibranching polymerization (ROMBP) of glycidol by slow monomer addition on partially deprotonated polyvalent 1,1,1-tris(hydroxyl-methyl) propane (TMP) as the starter [9].

dPG-Amidoglyceryl Succinyl Sulfate (dPG-ASuS)

dPG-amidoglyceryl succinyl sulfate (dPG-ASuS) (3) (see FIG. 3A) which contains a polar but comparably short and rigid linker including an ester and an amide functionality, offers the opportunity of acidic as well as enzymatic cleavage and was synthesized over three steps (FIG. 4A). Dendritic polyglycerol (1) was reacted with succinic anhydride for two days at room temperature in pyridine, acting as solvent and base to deprotonate dPG and initiate the ring opening of succinic anhydride. Ultrafiltration under addition of sodium chloride to avoid the precipitation of dPG-succinic acid gave dPG sodium succinate (dPG-Su, 6) in 75% yield with a full conversion (fully functionalized). dPG-amidoglyceryl succinate (dPG-ASu) (7) was prepared by a modified peptide coupling procedure from Pickaert et al. [10] with aminoglycerol, 1-ethyl-3-(3-dimethylaminopropyl)carbodiimide hydrochloride (EDC.HCl), and a catalytic amount of 4-(dimethyl-amino)pyridine (DMAP). Dialysis yielded the amide 7 in 85% with a degree of functionalization (dF) of 95%. Subsequent sulfation with $SO_3$.pyridine complex [3] gave dPG-amidoglyceryl succinyl sulfate (ASuS, 3) in 71% yield with a dF=63% as a highly water soluble colourless product.

dPG-Thioglyceryl Pentanoatyl Sulfate (dPG-TPS)

dPG-thioglyceryl pentanoatyl sulfate (dPG-TPS, 4) (see FIG. 3B) containing a very long, flexible and very hydrophobic linker including an ester functionality was synthesized over three steps (FIG. 4B). Dendritic polyglycerol (1) was reacted with an equimolar amount of pentenoyl chloride and an excess of triethylamine as base in DMF. dPG-pentenoate (8) was obtained in 92% yield with a dF=84%, as determined by $^1$H-NMR. Subsequent radical thiolene reaction of 8 with thioglycerol was performed under UV-radiation for 90 minutes at room temperature with 2,2-dimethoxy-2-phenylacetophenone (DMPA) as the photoinitiator. dPG-thioglyceryl pentanoate (dPG-TP, 9) was obtained in 77% yield with complete conversion as determined by $^1$H-NMR due to absent signals of the allyl group at 4.71-5.27 ppm and 5.54-5.96 ppm. Further sulfation of 9 with SO$_3$.pyridine complex gave dPG-TPS (4) in 92% yield with a dF=67%.

dPG-Thioglyceryl Methylpropanoatyl Sulfate (dPG-TMPS)

The implementation of a long, flexible and relatively hydrophobic linker containing a carbamate and an ester functionality was accomplished by the synthesis of dPG-thioglyceryl methylpropanoatyl sulfate (dPG-TMPS, 5) (see FIG. 3C). Whereas both, the ester and carbamate group represent acid labile moieties, the ester functionality could also be cleaved by enzymes like carboxylesterases. dPG-TMPS was synthesized over three steps with 50% of the linker (FIG. 4C). The carbamate 10 was prepared following a modified procedure from Bryant et al. [11]. In analogy dendritic polyglycerol (1) was reacted with 0.9 eq. of 2-isocyanato-ethyl methacrylate to give dPG-methacrylate (10) with a dF=50%, as determined by $^1$H-NMR. To avoid gel formation butyl-hydroxytoluene (BHT) was added and direct conversion of 10 to the corresponding glycidyl thioether by Michael-addition of thioglycerol was realized. dPG-thioglyceryl methyl propanoate (dPG-TMP, 11) was isolated in 62% yield over two steps due to partial polymerization of the intermediate 10. Complete conversion was determined by $^1$H-NMR due to the vanished signals of the methacrylate group at 5.55-5.57 ppm and 6.08-6.10 ppm. Subsequent sulfation with SO$_3$.pyridine gave dPG-thioglyceryl methylpropanoatyl sulfate (dPG-TMPS, 5) in 84% yield with a dF=78%.

Dendritic Polyglycerol Sulfate (dPGS)

Dendritic polyglycerol sulfate (dPGS, 2) was prepared as non-degradable analog to compare its biocompatibility and anti-inflammatory activity with the synthesized shell degradable compounds. Sulfation of dendritic polyglycerol with SO$_3$ pyridine gave dPGS with a dF=91% in 68% yield.

$^1$H-NMR analysis confirmed the intact structure of the degradable compounds after each reaction. Analytic data of the prepared polysulfates are summarized in Table 1.

TABLE 1

Specification of the prepared polysulfates 2-5 and the dPG scaffold 1.

| Polymer | # | $M_n$ [g mol$^{-1}$] | NS | dS [%] | $d_h \pm$ SD [nm] | PDI | $\zeta$-potential $\pm$ SD [mV] | IC$_{50}$ [nM] |
|---|---|---|---|---|---|---|---|---|
| dPG | 1 | 5,100 | — | — | 4.0 ± 0.4 | 0.22 | — | — |
| dPGS | 2 | 11,500 | 63 | 91 | 5.8 ± 0.6 | 0.28 | −18.6 ± 2.3 | 0.65 |
| dPG-ASuS | 3 | 25,500 | 84 | 63 | 6.4 ± 0.6 | 0.37 | −35.4 ± 3.0 | 1.3 |
| dPG-TPS | 4 | 25,900 | 85 | 67 | 7.4 ± 0.7 | 0.23 | −27.4 ± 4.6 | 0.65 |
| dPG-TMPS | 5 | 22,600 | 81 | 78 | 5.8 ± 0.6 | 0.21 | −25.7 ± 4.7 | 0.2 |

$M_n$ = Number average molecular weight calculated from the dF.
NS = Number of sulfate groups per polymer.
DS = Degree of sulfation determined by $^1$H-NMR and elemental analysis.
$d_h$ = Hydrodynamic diameter (mean ± standard deviation (SD)) by DLS in PBS (pH 7.4) from the size distribution by volume.
PDI = Polydispersity index (DLS).
$\zeta$-potential (mean ± SD) in 10 mM phosphate buffer (pH 7.4).
IC$_{50}$ values describe the compound concentration required to inhibit ligand binding of L-selectin functionalized Au nanoparticles.

Sulfated shell degradable polymers were synthesized with comparable molecular weights from 22,600 g mol$^{-1}$ up to 25,900 g mol$^{-1}$ and sizes between 5.8 nm and 7.4 nm. Sulfation of the precursors yielded highly water soluble anionic polymers with a degree of functionalization over 63% and similar numbers of sulfate groups ranging from 81 to 85 as determined by $^1$H-NMR and elemental analysis. $\zeta$-potential measurements showed surface charges between −26 mV and −35 mV. The slightly lower $\zeta$-potential of dPG-ASuS (3) is probably caused by not fully functionalized succinic acid residues of the precursor, since dPG carboxylates were shown to exhibit a more negative surface charge compared to sulfates [3]. Using the same polyglycerol scaffold, non-degradable dPGS (2) in contrast was prepared with a lower molecular weight of 11,600 g mol$^{-1}$ and a size of 5.8 nm. With a degree of sulfation of 91%, dPGS contained 63 functional groups and a higher $\zeta$-potential of −18.6 mV compared to the shell degradable compounds.

L-Selectin Inhibition

The anti-inflammatory potential of the prepared polysulfates was estimated by the quantification of L-selectin inhibition, determined by a concentration dependent, competitive SPR-based binding assay, which was previously described in detail [12]. In short, L-selectin-IgG chimeras were coated on Au nanoparticles to imitate L-selectin expressing leukocytes. L-selectin ligands including Sialyl-Lewis$^x$ (sLe$^x$, 20 mol %) and sulfated tyrosine (sTyr, 5 mol %), were immobilized on the surface of a BIAcore sensor chip to mimic the endothelium surface. Then the L-selectin coated Au nanoparticles were passed over the sensor chip resulting in a binding signal, which was set to 100% and served as reference. Subsequently, L-selectin functionalized nanoparticles were pre-incubated with a potential inhibitor and passed over the surface of the chip. The inhibitor concentration dependent reduction of the binding signal was recorded and calculated as relative binding of the reference. The concentration that caused a 50% reduced binding was quoted as IC$_{50}$ value. Each inhibitor concentration was applied at least in triplicate. This reproducible in vitro experiment mimics the leukocyte binding to endothelial surface in vivo in the presence of a potential inhibitor in good approximation. $IC_{50}$ values of the prepared polysulfates are shown in Table 1.

For all degradable compounds $IC_{50}$ values in the low nano to high picomolar range were found, comparable to the non-degradable dendritic polyglycerol sulfate, which confirms their high anti-inflammatory activity. Whereas dPG-TPS (4) and dPGS (2) showed similar $IC_{50}$ values of 0.65 nM, dPG-ASuS (3) binds L-selectin one order of magnitude less (1.3 nM). However, the lower (but still very suited) $IC_{50}$ value of dPG-TMPS (5) of 0.2 nM demonstrates that the L-selectin binding affinity is not only dependent on the number of sulfate groups and molecular weight but also depends on the nature of the linker, since all degradable compounds were prepared with comparable characteristics regarding their molecular weight and number of functional groups.

Blood Coagulation

Figure 5:
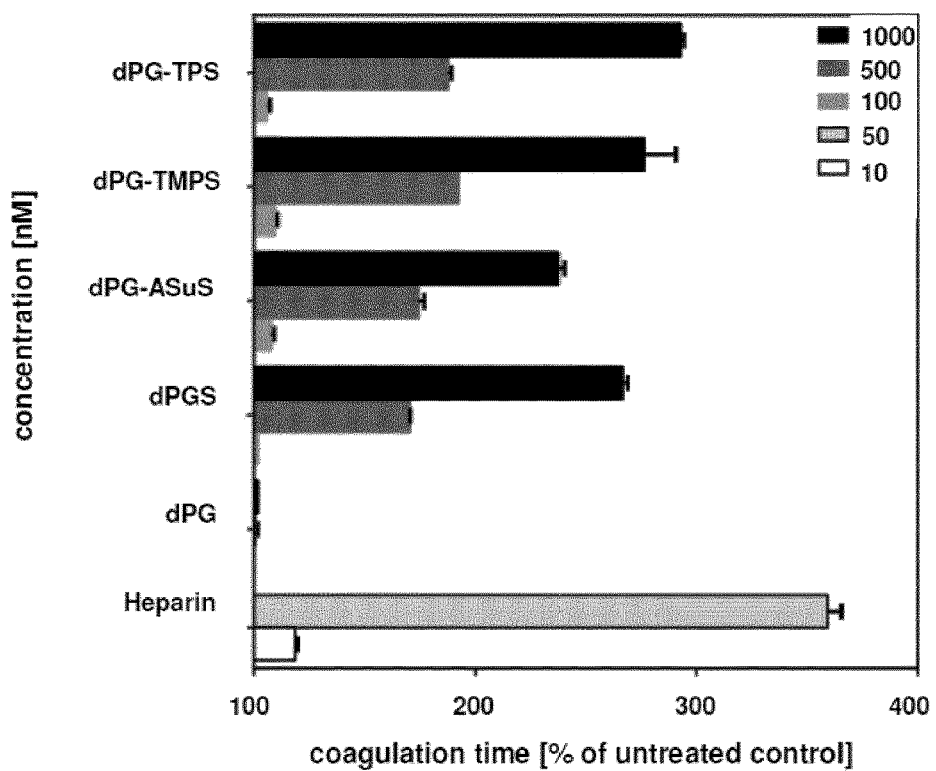
FIG. 5 shows concentration dependent coagulation times of different polyglycerol compounds.

To confirm the biocompatibility of the shell degradable polysulfates their influence on blood coagulation and complement activation was investigated and compared to non-degradable dPGS. The anticoagulant activity of the prepared polymers was evaluated by activated partial thromboplastin time (APTT) clotting assay using citrated human platelet poor plasma (PPP). Fresh PPP was incubated with the sulfates 2-5 or neutral dPG (1), in concentrations between 100 nM and 1 µM. Heparin was used as standard compound and was added in concentrations of 10 nM and 50 nM. After incubation, the clotting time was determined and compared to untreated control which was set to 100%. As depicted in FIG. 5, prepared polysulfates showed a negligible influence on the coagulation time at a concentration of 100 nM compared to heparin, which already exhibits a slightly higher anti-coagulant activity at 10 nM.

However, with increasing concentrations all polysulfates were found to prolong the APTT, whereas the neutral dendritic polyglycerol did not influence the blood coagulation at all. At 500 nM the blood clot times were almost doubled whereas a concentration of 1 µM lead to a threefold prolonged APTT. The comparable clotting time patterns of all polysulfates indicate that the linker itself does not have a significant influence on the blood coagulation. Still, the prepared compounds showed a much lower anticoagulant activity even at the highest concentration (1 µM) compared to heparin which lead to a 3.5-fold prolonged coagulation time at a concentration of 50 nM.

Complement Activation

Since the activation of the complement is known to cause severe problems including multiple organ dysfunctions or septic shocks due to the release of pro-inflammatory complement proteins, the anaphylatoxins C3a and C5a [13], interactions of the prepared polysulfates with the complement system have to be taken into account. The complement activation in human serum was tested for the immunoglobin dependent classical pathway with an ELISA-based method. Serum samples were incubated with the test compounds in concentrations of 50 nM to 2.5 µM.

Figure 6:
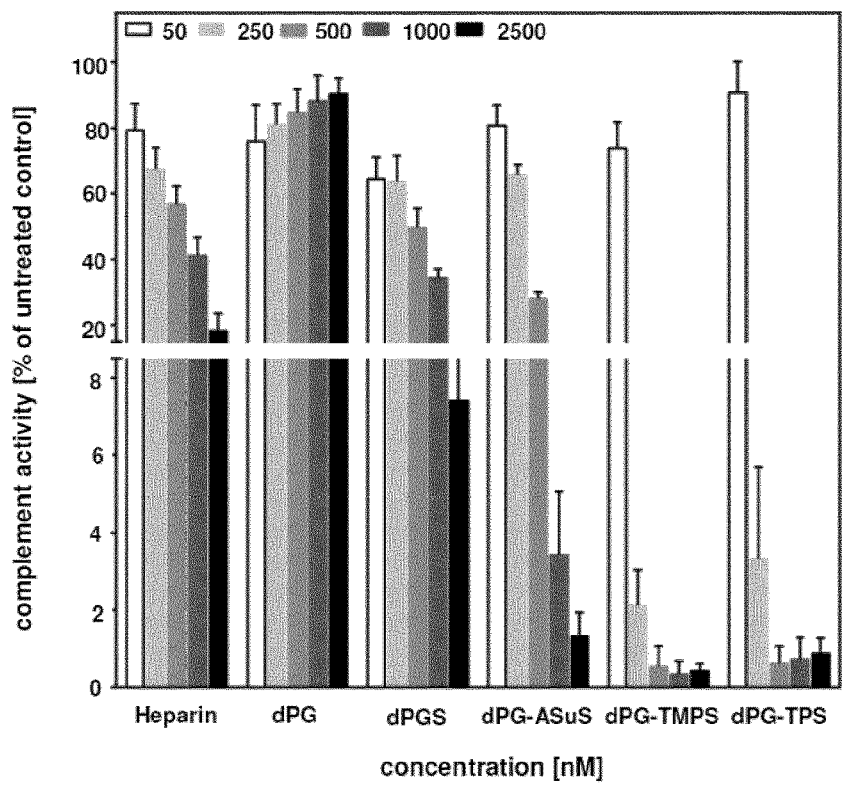
FIG. 6 shows levels of concentration dependent complement activation of different polyglycerol compounds.

The level of complement activity is stated as percentage of the untreated serum control in FIG. 6. Heparin was used as reference. Complement activity is given as percent of the untreated control. All tested compounds were found to decrease the complement activation. Whereas neutral dPG (1) showed only slightly reduced activity even at high concentrations of around 80% of the control, the sulfated compounds exhibited a much stronger reduction of the complement activation in a concentration dependent manner. dPGS (2) showed similar activities compared to heparin up to a concentration of 1 µM and a higher complement activation at 2.5 µM. For dPG-ASuS (3) a comparable activity was found concentrations of 50 nM and 250 nM, but enhanced reduction to 30% and 3% activity at concentrations of 500 nM and 1 respectively. Almost full inhibition of complement was observed at a concentration of 2.5 µM. Surprisingly, dPG-TPS (4) and dPG-TMPS (5) performed even better, only 2.5% complement activity was already found at a concentration of 250 nM and almost total inhibition at 500 nM. These findings might be related to the longer and more flexible linker between the sulfate groups and the polyglycerol backbone of the degradable polysulfates compared to dPGS and heparin, which could increase the probability of interactions with proteins of the complement cascade. Moreover, both dPG-TMPS (5) and dPG-TPS (4) contain a thioether moiety within their linker which also seems to play an important role in protein targeting. The results clearly indicate that the prepared biodegradable polysulfates can be used as potent complement inhibitors of the classical pathway for the treatment of inflammation associated diseases.

In Vitro Degradation Studies

Degradation of the new polysulfates was investigated over a period of 4 weeks in PBS buffer under neutral (pH 7.4) and acidic (pH 5.0) conditions. Enzymatic degradation was analyzed with carboxylesterase I (CES I). Latter is found in high concentrations in the liver and was used due to the known accumulation of dPGS in hepatic Kupffer cells [7, 8]. Since the synthesized shell degradable polymers contain linkers that exhibit esters and additional amide or carbamate moieties, hydrolytic or enzymatic cleavage of different functional groups could take place.

However, as evident from $^{13}$C-NMR analysis only ester hydrolysis proceeded, leading to sulfated carboxylic acids of low molecular weight and respective high molecular weight alcohols.

Figure 7A:
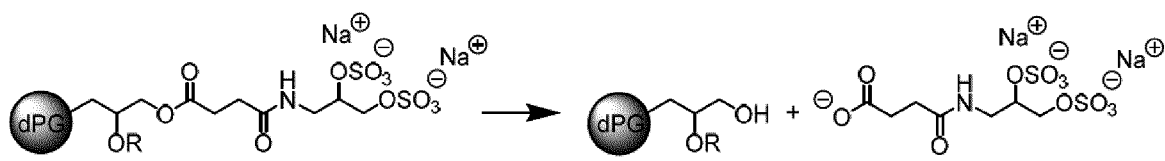
FIG. 7A shows a reaction scheme of the degradation of a polyglycerol derivative bearing residue R of FIG. 3A.
Figure 7B:
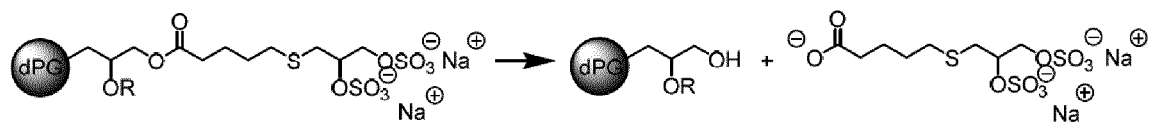
FIG. 7B shows a reaction scheme of the degradation of a polyglycerol derivative bearing residue R of FIG. 3B.
Figure 7C:
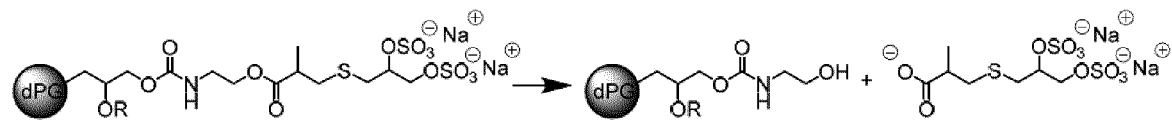
FIG. 7C shows a reaction scheme of the degradation of a polyglycerol derivative bearing residue R of FIG. 3C.

FIGS. 7A to 7C show reaction schemes of the degradation of the three polyglycerol compounds dPG-ASuS (3), dPG-TPS (4) and dPG-TMPS (5).

Degradation of the polysulfates was monitored by $^1$H-NMR or by elemental analysis in case of dPGS. Occurring spikes in the $^1$H-NMR spectra in the area of broad polymer and linker signals as well as the presence of new peaks indicated hydrolysis of the compounds. In case of dPG-ASuS (3) sharp peaks arised over time between 3.59 ppm and 4.30 ppm while a new signal at 2.77 ppm appeared due to the α-CH$_2$ group of the formed acid. For dPG-TMPS (5) spikes between 3.19 ppm and 4.71 ppm were observed as well as broadening of the signal between 2.53 ppm and 3.04 ppm, latter peaks caused by the methyl-neighboring —CH-group and the two methylen bridges next to the thioether. The appearance of multiple —CH$_3$ signals indicates the presence of different methyl species due to the cleavage of the ester. In comparison, degradation of the carbamate function would show much less influence on the methyl group. For dPG-TPS (4) sharp signals between 2.18 ppm and 4.75 ppm were found over time as well as shrinking of the peak between 4.13 ppm and 4.75 ppm. Ester cleavage was also quantified by $^1$H-NMR.

In case of dPG-TMPS (5) and dPG-TPS (4) the integral ratios of areas that remained the same were compared to that of signals which decreased over time. For dPG-TMPS (5) the integral of the methyl group at 1.24 ppm was determined relative to that from 4.50 ppm to 3.28 ppm. In case of dPG-TPS (4) the integral between 2.07 ppm and 1.21 ppm was compared to that of the diminishing peak between 4.57 ppm and 4.13 ppm. Since dPG-ASuS (3) showed no significant decrease of any signal, the integral of the arising peak at 2.77 ppm was subtracted from that of the peak caused by the $CH_2$ groups between the ester and amide moiety. The integral ratio of the respective non-treated polymer was set to 100%, and changes in the ratio were calculated as %, directly giving the content of ester. Because the cleavage of sulfate groups in case of dPGS (2) would not show significant differences in the $^1$H-NMR spectra and hence no precise quantification of degradation would be possible, the sulfur content was determined by elemental analysis after purification via GPC column.

Figure 8A:
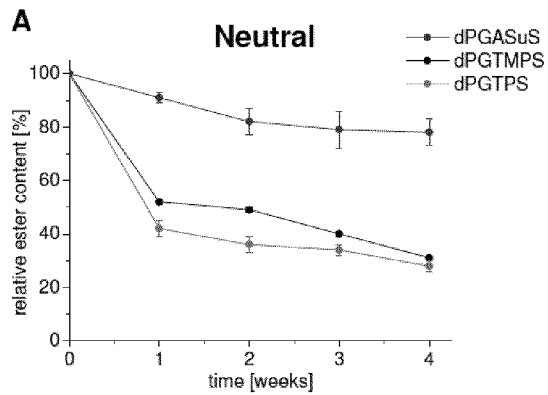
FIG. 8A shows a first degradation profile of different polyglycerol derivatives.
Figure 8B:
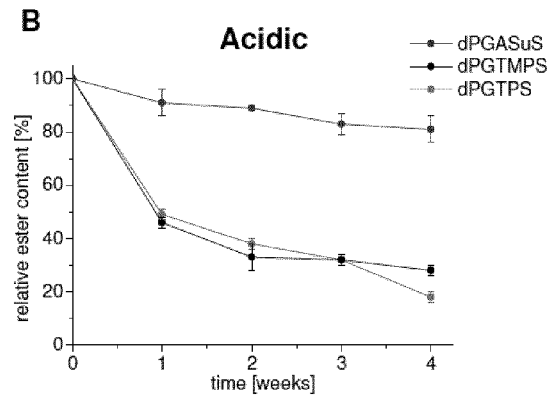
FIG. 8B shows a second degradation profile of different polyglycerol derivatives.
Figure 8C:
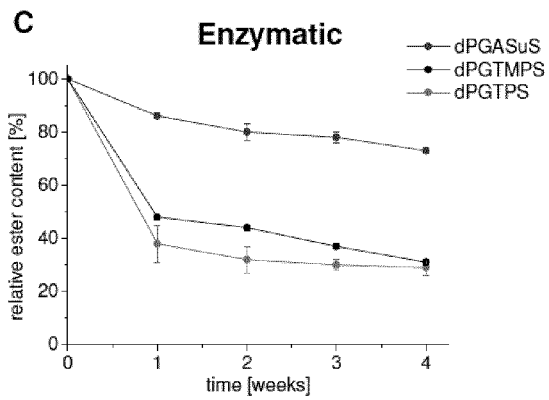
FIG. 8C shows a third degradation profile of different polyglycerol derivatives.
Figure 8D:
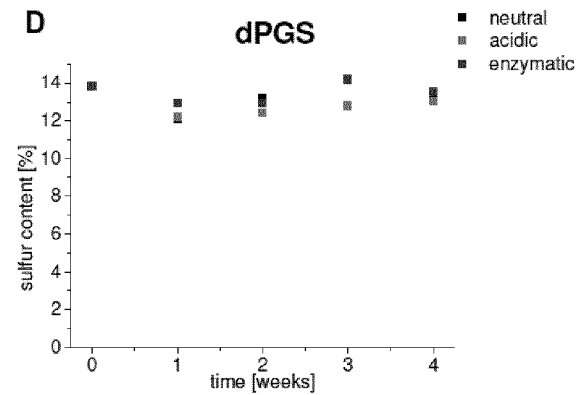
FIG. 8D shows a forth degradation profile of polyglycerol sulfate.

The stability of the polysulfates at different conditions is depicted in FIGS. 8A to 8D. As determined by elemental analysis after purification by size exclusion chromatography (SEC), dPGS (2) is stable over 4 weeks (FIG. 8D). In contrast, for dPG-ASuS (3) slow degradation was observed, whereas dPG-TMPS (5) and dPG-TPS (4) were found to undergo much faster decomposition. In case of dPG-ASuS (3) around 80% of the esters remained over 4 weeks, while approximately half of the linkers were already cleaved within 1 week in case of dPG-TMPS (5) and dPG-TPS (4). However, complete decomposition of the ester linkages was not observed for any of the cleavable polysulfates. Surprisingly, no relevant influence of the pH value on the degradation process was obvious, although esters are known to underlie acidic rather than neutral cleavage. Moreover, the data shown indicate that carboxylesterase I does not contribute to the degradation of the compounds which might be due to electrostatic interactions of the enzyme with sulfate groups of the substrate or might be caused by the tightly packed structure of the polymers that may shield the enzyme from acting. Nevertheless, the prepared shell cleavable polysulfates can be considered as potent degradable dPGS-analogs and hence are interesting scaffolds for long term treatment of inflammation-related diseases.

Summarizing, the synthesis of highly water soluble shell degradable polysulfates via implementation of hydrolytically or enzymatically cleavable linkers into a biocompatible dendritic polyglycerol (dPG) backbone and further sulfation is disclosed. The compounds were prepared with similar molecular weights as well as numbers of sulfate groups and contained either only ester groups (dPG-thioglyceryl pentanoatyl sulfate, dPG-TPS) or additional amide (dPG-amidoglyceryl succinyl sulfate, dPG-ASuS) and carbamate functionalities (dPG-thioglyceryl methylpropanoatyl sulfate, dPG-TMPS). All polymers were investigated regarding their degradation behavior, blood coagulation properties, complement activation and L-selectin binding in vitro. Dendritic polyglycerol sulfate (dPGS) was used as stable analog for comparison. Very slow degradation was found for dPG-ASuS whereas in case of dPG-TPS and dPG-TMPS a much faster decomposition was observed under all test conditions compared to the cleavage-resistant dPGS. As determined by an APTT assay, all prepared polysulfates showed a comparable clotting time pattern similar to dPGS and only a slight influence on blood coagulation up to a concentration of 100 nM. In marked contrast complement activation was strongly influenced by dPG-TMPS and dPG-TPS. Total inhibition was observed at nanomolar concentrations. A further anti-inflammatory activity was determined via a competitive SPR-based L-selectin binding assay. For all degradable compounds $IC_{50}$ values in the low nano to high picomolar range were found, comparable to dPGS. The binding inhibition increased in the order dPG-ASuS<dPG-TPS=dPGS<dPG-TMPS confirming the high anti-inflammatory activity of the newly prepared compounds. The studies show that the shell degradable polysulfates are potent cleavable dPGS-analogs and hence are suited compounds for the long term treatment of chronic inflammations or can be applicable in tissue engineering due to their low anti-coagulant and high anti-inflammatory properties. As remarkably strong inhibitors of the complement, theses scaffolds can also be considered as a new class of anti-complement therapeutics with desirable pharmacologic properties to prevent the progress of tissue damage within inflammatory diseases.

In the following, more details on the performed experiments are disclosed.

Reactions including air or moisture sensitive substances were carried out under argon atmosphere using flame-dried glassware and anhydrous solvents. Chemicals were reagent grade and were used without further purification. Dialysis was performed in benzoylated cellulose tubings (molecular weight cut off (MWCO): 2000 g mol$^{-1}$) changing the solvent at least 8 times over a period of 72 h. Ultrafiltration was performed in solvent-resistant stirred cells with PLAC regenerated cellulose membranes (MWCO 1000 g mol$^{-1}$). $^1$H- and $^{13}$C-NMR spectra were recorded on a Jeol ECX 400 spectrometer operating at 400 and 101 MHz or on a Bruker Biospin Avance 700 spectrometer operating at 700 and 176 MHz. Chemical shifts δ were reported in ppm using the deuterated solvent peak as the internal standard (CDCl$_3$: δ ($^1$H)=7.26 ppm, δ ($^{13}$C)=77.16 ppm; CD$_3$OD: δ ($^1$H)=3.31 ppm, δ ($^{13}$C)=49.00 ppm; D$_2$O: δ ($^1$H)=4.79 ppm). $^{13}$C-Spectra were broadband proton decoupled. Multiplicity of NMR-signals is listed as s (singlet) or m (multiplet). Signal assignment was partially performed by two-dimensional NMR spectra (COSY, HMQC, HMBC). IR measurements were recorded on a Nicolet Avatar 320 FT-IR equipped with a DTGS detector from 4000 to 650 cm$^{-1}$ and evaluated with the software EZ OMNIC ESP. Wavenumbers $v_{max}$ were reported in cm$^{-1}$, the intensities of absorption bands were assigned as strong (s), medium (m), and weak (w). Elemental analysis was performed on a VARIO EL III instrument using sulfanilic acid as standard. DLS and ζ-potential measurements were carried out on a Zetasizer Nano ZS equipped with a 4 mW He—Ne laser (λ, =633 nm, NIBS) operating with a 173° scattering angle (backscatter). Particle size was measured in UV-transparent disposable cuvettes (8.5 mm) at 25° C. Samples were dissolved in Dulbecco's PBS (DPBS, 150 mM, 1x, without Ca$^{2+}$, Mg$^{2+}$, pH=7.4) at a concentration of 2 mg ml$^{-1}$. The solutions were filtered once trough a 0.45 μm PTFE syringe filter and twice trough a 0.2 μm PTFE syringe filter. Samples were equilibrated for 60 seconds at 25° C.; subsequently, the measurement was performed with 15 scans per sample. The stated values are the mean of at least 15 independent measurements. For ζ-potential measurements samples were dissolved in phosphate buffer (PB, 10 mM, pH 7.4) at a concentration of 1 mg ml$^{-1}$. The solutions were filtered once through a 0.2 μm Cellulose acetate syringe filter and measured by applying an electric field across the polymer at 25° C. in folded DTS 1060 capillary cells. Data evaluation was performed with Malvern Zetasizer Software 6.12. The stated values and standard deviations are the mean of at least five independent measurements with 15 scans each and are based on the Smoluchowski model. UV irradiation was performed using an USHIO super high pressure mercury lamp (USH 102d; 100 W, 0.12 Amps) without a filter.

Degradation Studies

Degradation studies were performed in PBS buffer with pH 5.0 or pH 7.4, respectively over 4 weeks at 37° C. with shaking at 200 rpm using total sample concentrations of 2 μmol ml$^{-1}$. pH values were kept constant over time by addition of NaOH if needed. For enzymatic degradation studies samples were dissolved in PBS buffer with pH 7.4 and Carboxylesterase I (CES I, isoform b, human, 1000 U ml$^{-1}$) was added to a total concentration of 1.86 units ml$^{-1}$. Every 4 days 50% of the enzyme activity was added since 50% of the activity is lost after 4 days as shown in an enzyme activity assay. After each time point (7, 14, 21, 28 days) an aliquot of 500 μL was removed, the pH value was adjusted to 7.0 and the solvent was evaporated. The residue was dissolved in D$_2$O and the solution was filtered through a 0.2 μm PTFE syringe filter (VWR). In case of enzymatic degradation additionally bis(4-nitrophenyl)phosphoric acid (BNPP) was added to a total concentration of 1 mM to inhibit the enzyme. The progress of degradation was either determined by $^1$H-NMR spectra as content of esters or by elemental analysis of the sulfur content (see supporting information). Degradation studies were performed as duplicates and samples were stored at −10° C.

Synthesis

Dendritic Polyglycerol (dPG) with a molecular weight of M$_n$=5,100 g mol$^{-1}$ bearing in average ~69 hydroxyl groups per molecule, a PDI<1.8 and a degree of branching of ~60% was synthesized according to literature via anionic ring opening polymerization of glycidol using 1,1,1-tris(hydroxymethyl)propane (TMP) as the starter [9]. Molecular weights of further derivatives were calculated from the particular conversion as determined by $^1$H-NMR spectroscopy or from the sulfur content obtained by elemental analysis.

General Procedure for Sulfation

Sulfated polymers were prepared according to Turk et al. [1]. In brief, the polyol was dissolved in dry DMF, heated to 60° C. and a solution of SO$_3$.pyridine complex (1.2 eq. per OH group) in dry DMF was added dropwise over 2 hours. After addition the mixture was stirred over night (o.n.) at 60° C. Then aq. NaOH (2 M, 0.9 eq. per SO$_3$.pyridine complex) and water were added, and the pH was adjusted to 7 by addition of aq. NaOH (10%). The solvent was evaporated and the crude product was subjected to ultrafiltration in water. After freeze-drying the product was obtained as a colorless solid.

Dendritic Polyglycerol Sulfate (dPGS) (2)

dPG sulfate was synthesized according to the general procedure for sulfation by applying dendritic polyglycerol (5,100 g mol$^{-1}$, 69 OH groups). The compound was obtained as colorless solid after freeze-drying. M$_n$ (dPG-core)=5,100 g mol$^{-1}$, M$_n$=11,600 g mol$^{-1}$, dF=91%, yield: 74%. $^1$H-NMR (400 MHz, D$_2$O): δ=3.45-4.15 (m, 5H, PG-backbone); 4.15-4.48 (m, 2H, C$_{prim}$. H$_2$OSO$_3$); 4.59-4.89 (m, 1H, C$_{sec}$.HOSO$_3$) ppm.

Dendritic Polyglycerol Sodium Succinate (dPG-Su) (6)

To a solution of dPG (5.00 g, 0.98 mmol, 67.62 mmol OH groups) in pyridine (30 ml) succinic anhydride (7.44 g, 74.36 mmol, 1.1 eq. per OH group) was added at room temperature. After stirring for 2 d at room temperature the solvent was evaporated. The residue was dissolved in water and the pH value was adjusted to 7 by addition of aq. NaOH (10%). The crude product was subjected to ultrafiltration in water and addition of small amounts of NaCl for the first three cycles to avoid precipitation of dPG-succinic acid. Freeze drying yielded the compound as a colorless solid. M$_n$ (dPG-core)=5,100 g mol$^{-1}$, M$_n$=13,600 g mol$^{-1}$, dF=100%, yield: 75%

$^1$H-NMR (400 MHz, D$_2$O): δ=2.43-2.85 (m, 4H, CH$_2$CH$_2$COOR, CH$_2$CH$_2$COOR); 3.26-4.48 (m, 5H, PG-backbone); 4.99-5.35 (m, 0.5H, PG-backbone) ppm. $^{13}$C-NMR (176 MHz, D$_2$O): δ=30.0 (CH$_2$CH$_2$COOR); 31.0 (CH$_2$CH$_2$COONa); 63.0, 63.9, 65.7, 67.8, 68.1, 69.3, 69.8, 70.7, 71.0, 71.8, 77.2, 78.3 (PG-backbone); 174.6, 175.1 (COOR); 179.3 (COONa) ppm. IR νmax: 807 (m), 844 (m), 873 (m), 999 (s), 1079 (s), 1150 (s), 1202 (s), 1254 (s), 1312 (m), 1368 (s), 1403 (s), 1574 (s), 1727 (s), 2352 (w), 2879 (m), 2920 (m), 3398 (m) cm$^{-1}$.

Dendritic Polyglycerol Amidoglyceryl Succinate (dPG-ASu) (7)

1-Aminoglycerol (5.54 ml, 6.59 g, 70.00 mmol, 2.0 eq. per acid group) was dissolved in water (50 ml) and the pH value of the resulting solution was adjusted to 8 by addition of HCl (1 M). Then DMAP (0.93 g, 7.61 mmol, 0.25 eq. per acid group) was dissolved in water (20 ml), the pH value was adjusted to 8 by means of HCl (1 M), and dPG succinate sodium salt (6.00 g, 0.44 mmol, 30.50 mmol acid groups) was added. After addition of EDC.HCl (5.85 g, 30.50 mmol, 1.0 eq. per acid group) 1-Aminoglycerol in water was added immediately and the mixture was stirred over night at room temperature. Dialysis in water yielded the product as a colorless honey like oil. M$_n$ (dPG-core)=5,100 g mol$^{-1}$, M$_n$=17,000 g mol$^{-1}$, dF=95%, yield: 85%

$^1$H-NMR (400 MHz, D$_2$O): δ=2.36-2.77 (m, 4H, CH$_2$CH$_2$COOR, CH$_2$CH$_2$COOR); 3.05-4.41 (m, 10H, PG-backbone, aminoglycerol), 4.86-5.37 (m, 1H, PG-backbone) ppm. $^{13}$C-NMR (176 MHz, D$_2$O): δ=29.3 (CONHCH$_2$CH$_2$); 30.1 (CH$_2$CH$_2$COOR, CH$_2$CH$_2$COONa); 41.8, 42.7 (CONHCH$_2$CHCH$_2$); 63.3 (CONHCH$_2$CHCH$_2$); 65.8, 67.8, 68.0, 69.6 (PG-backbone); 70.3 (CONHCH$_2$CHCH$_2$); 71.8, 72.2, 73.7, 77.0, 78.2, 79.5 (PG-backbone); 174.5 (CONHR, COOR); 179.4 (COONa) ppm. IR ν$_{max}$: 800 (w), 869 (w), 932 (w), 1000 (m), 1083 (s), 1161 (s), 1206 (m), 1240 (m), 1384 (m), 1408 (m), 1552 (m), 1552 (m), 1650 (s), 1698 (m), 1729 (s), 2876 (m), 2926 (m), 3323 (m) cm$^{-1}$.

Dendritic Polyglycerol Amidoglyceryl Succinyl Sulfate (dPG-ASuS) (3)

dPG-amidoglyceryl succinyl sulfate was synthesized according to the general procedure for sulfation by applying dPG-amidoglyceryl succinate (17,000 g mol$^{-1}$, 132 OH groups). The compound was obtained as colorless solid after freeze-drying. M$_n$ (dPG-core)=5,100 g mol$^{-1}$, M$_n$=25,500 g mol$^{-1}$, dF=63%, yield: 71%

$^1$H-NMR (400 MHz, D$_2$O): δ=2.46-2.88 (m, 4H, CH$_2$CH$_2$COOR, CH$_2$CH$_2$COOR); 3.16-4.75 (m, 10H, PG-backbone, aminoglycerol), 5.14-5.43 (m, 0.5H, PG-backbone) ppm. $^{13}$C-NMR (176 MHz, D$_2$O): δ=29.4 (CONHCH$_2$CH$_2$); 30.3 (CH$_2$CH$_2$COOR); 31.6 (CH$_2$CH$_2$COONa); 39.7, 43.0 (CONHCH$_2$CHCH$_2$); 63.4 (CONHCH$_2$CHCH$_2$); 66.8, 67.4, 68.4 (PG-backbone); 69.9 (CONHCH$_2$CHCH$_2$); 71.9, 75.3, 77.0, 78.3 (PG-backbone); 174.2 (CONHR); 174.5 (COOR); 180.5 (COONa) ppm. IR ν$_{max}$: 771 (m), 936 (m), 1008 (m), 1034 (m), 1071 (m), 1215 (s), 1408 (w), 1462 (w), 1557 (w), 1652 (m), 1698 (m), 1729 (m), 2883 (w), 2931 (w), 3479 (w) cm$^{-1}$.

Dendritic Polyglycerol Pentenoate (8)

To a solution of dPG (2.08 g, 0.39 mmol, 27.06 mmol OH groups) in DMF (20 ml) was added NEt$_3$ (4.8 ml) and BHT (0.33 g, 10 wt % of acid chloride). After cooling to 0° C., pentenoyl chloride (3.0 ml, 3.21 g, 27.06 mmol) was added over 30 min. The resulting solution was stirred over night in the melting ice bath, methanol (2.0 ml) was added and stirred for additional 5 min. Afterwards the solvent was removed, the residue was dissolved in chloroform, filtered and dialyzed. Evaporation yielded the product as a brown oil. M$_n$ (dPG-core)=5,100 g mol$^{-1}$, M$_n$=9,900 g mol$^{-1}$, dF=84%, yield: 92%.

$^1$H-NMR (400 MHz, D$_2$O): δ=1.96-2.96 (m, 4H, C=OCH$_2$CH$_2$, C=OCH$_2$CH$_2$); 2.96-4.47 (m, 6H, PG-backbone); 4.71-5.27 (m, 2H, CH=CH$_2$); 5.54-5.96 (m, 1H, C H=CH$_2$) ppm. $^{13}$C-NMR (176 MHz, D$_2$O): δ=27.3, 28.7, 28.8 (C=OCH$_2$CH$_2$); 31.2, 32.1, 33.2, 33.3, 33.4, 33.5 (C=OCH$_2$CH$_2$); 58.2, 62.7, 63.6, 65.3, 68.6, 69.6, 70.0, 71.2, 71.4, 71.6, 72.1, 72.5, 72.7, 78.7 (PG-backbone); 115.6, 117.6 (CH=CH$_2$); 134.1, 136.5, 136.6 (CH=CH$_2$); 168.5, 168.7, 172.2, 172.5, 172.8, 173.0 (C=OCH$_2$CH$_2$) ppm.

Dendritic Polyglycerol Thioglyceryl Pentanoate (dPG-TP) (9)

To a solution of dPG pentenoate (3.43 g, 0.35 mmol, 20.19 mmol ene groups) in chloroform (80 ml) was added thioglycerol (2.1 ml, 2.60 g, 24.23 mmol 1.2 eq. of ene groups) and 2,2-dimethoxy-2-phenylacetophenone (51.5 mg, 1.5 wt % of dPG pentenoate). The solution was degassed 3 times (freeze-pump-thaw) and irradiated with UV light for 90 min at room temperature. The solvent was removed, the residue was dissolved in methanol and dialyzed in methanol. Evaporation yielded the product as brown honey-like gel. $M_n$ (dPG-core)=5,100 g mol$^{-1}$, $M_n$=17,200 g mol$^{-1}$, dF=100%, yield: 77%.

$^1$H-NMR (400 MHz, D$_2$O): δ=1.24-2.13 (m, 4H, C=OCH$_2$CH$_2$, C=OCH$_2$CH$_2$CH$_2$); 2.17-3.04 (m, 6H, C=OCH$_2$CH$_2$, SCH$_2$CH$_2$, SCH$_2$CH); 3.42-4.62 (m, 9H, PG-backbone, SCH$_2$CHOH, SCH$_2$CHCH$_2$) ppm. $^{13}$C-NMR (176 MHz, D$_2$O): δ=23.7, 25.1 (C=OCH$_2$CH$_2$); 28.4, 30.1 (C=OCHCH$_2$CH$_2$); 33.2 (SCH$_2$CH$_2$); 34.6 (C=O CH$_2$CH$_2$); 36.3 (SCH$_2$CH); 64.0, 65.0 (PG-backbone); 66.0 (SCH$_2$CHCH$_2$); 66.8, 69.5, 69.7, 70.6, 71.0, 71.2 (PG-backbone); 72.8 (SCH$_2$CH); 73.7, 74.0, 78.7, 80.0 (PG-backbone); 170.8, 174.6, 174.9, 175.1, 175.4 (C=OCH$_2$CH$_2$) ppm. IR $v_{max}$: 752 (w), 880 (m), 927 (m), 1028 (s), 1069 (s), 1173 (m), 1256 (m), 1343 (w), 1411 (s), 1453 (w), 1730 (s), 2521 (w), 2871 (m), 2918 (m), 3379 (m) cm$^{-1}$.

Dendritic Polyglycerol Thioglyceryl Pentanotyl Sulfate (dPG-TPS) (4)

dPG-thioglyceryl pentanoatyl sulfate was synthesized according to the general procedure for sulfation by applying dPG-thioglyceryl pentanoate (17,200 g mol$^{-1}$, 127 OH groups). The compound was obtained as colorless solid after freeze-drying. $M_n$ (dPG-core)=5,100 g mol$^{-1}$, $M_n$=25,900 g mol$^{-1}$, dF=67%, yield: 92%.

$^1$H-NMR (400 MHz, D$_2$O): δ=1.22-2.16 (m, 4H, C=OCH$_2$CH$_2$, C=OCH$_2$CH$_2$CH$_2$); 2.16-3.15 (m, 6H, C=OCH$_2$CH$_2$, SCH$_2$CH$_2$, SCH$_2$CH); 3.19-4.75 (m, 9H, PG-backbone, SCH$_2$CHOSO$_3$, SCH$_2$CHCH$_2$) ppm. $^{13}$C-NMR (176 MHz, D$_2$O): δ=22.3, 23.5 (C=OCH$_2$CH$_2$); 26.7, 28.3 (C=OCHCH$_2$CH$_2$); 30.9, 31.7 (SCH$_2$CH$_2$); 33.5 (S CH$_2$CH); 34.8 (C=OCH$_2$CH$_2$); 58.0, 61.9, 63.2 (PG-backbone); 67.7 (SCH$_2$CHCH$_2$); 68.3, 68.6, 69.9, 70.7, 71.9, 75.6 (PG-backbone); 76.5 (SCH$_2$CH); 78.3 (PG-backbone); 174.8, 175.5 (C=OCH$_2$CH$_2$) ppm. IR $v_{max}$: 685 (w), 805 (w), 864 (m), 927 (m), 997 (s), 1045 (s), 1170 (s), 1198 (s), 1411 (w), 1455 (w), 1489 (w), 1634 (w), 1709 (m), 2871 (m), 2929 (m), 3381 (m) cm$^{-1}$.

Dendritic Polyglycerol Methacrylate (10)

To a solution of dPG (2.69 g, 0.53 mmol, 36.39 mmol OH groups) and BHT (0.50 g, 2.27 mmol, 10 wt % of isocaynatoethyl methacrylate) in DMF (15 ml) was added 2-isocyanato-ethyl methacrylate (4.62 ml, 5.08 g, 32.75 mmol, 0.9 eq. per OH group) over 30 min at 60° C. The resulting mixture was stirred over night at room temperature and was directly used in the next step without purification to avoid uncontrolled polymerization the product. $M_n$ (dPG-core)=5, 100 g mol$^{-1}$, $M_n$=10,500 g mol$^{-1}$, dF=50%, yield: n.d.

$^1$H-NMR (400 MHz, CDCl$_3$): δ=1.90 (s, 3H, CH$_3$); 3.09-4.27 (m, 14H, dPG-backbone, NHCH$_2$CH$_2$, NHCH$_2$C H$_2$), 5.56 (s, 1H, CCH$_2$), 6.09 (s, 1H, CCH2) ppm. $^{13}$C-NMR (176 MHz, CCl$_3$): δ=18.3 (CH$_3$); 40.1 (NHCH$_2$); 62.0 (dPG-backbone); 63.7 (NHCH$_2$CH$_2$); 66.1, 68.9, 69.5, 71.3, 72.7, 73.8, 78.7, 80.1 (PG-backbone); 126.2 (CH$_3$CCH$_2$); 136.0 (CH$_3$CCH$_2$); 156.5, 156.9 (NHC=O); 167.4 (CH$_3$CC=O) ppm. IR $v_{max}$: 666 (w), 731 (m), 753 (m), 816 (w), 863 (w), 912 (m), 944 (m), 1045 (s), 1095 (s), 1159 (s), 1255 (m), 1297 (m), 1388 (w), 1405 (w), 1454 (m), 1533 (m), 1637 (w), 1667 (m), 1709 (s), 2245 (w), 2342 (w), 2360 (w), 2875 (w), 2926 (w), 3355 (m) cm$^{-1}$.

Dendritic Polyglycerol Thioglyceryl Methylpropanoate (dPG-TMP) (11)

To a solution of dPG-methacrylate (0.53 mmol, 18.55 mmol methacrylate groups, 50% linker) in DMF was added NEt$_3$ (0.6 ml) and thioglycerol (6.4 ml, 8.03 g, 74.20 mmol, 4.0 eq. per methacrylate group). After stirring over night at room temperature the solvent was evaporated and the residue was dissolved in methanol. After filtration the filtrate was dialyzed in methanol. Evaporation yielded the product as a colorless gel. $M_n$ (dPG-core)=5,100 g mol$^{-1}$, $M_n$=14, 300 g mol$^{-1}$, dF=100%, yield: 62% over two steps.

$^1$H-NMR (400 MHz, CD$_3$OD): δ=1.25 (s, br, 3H, CH$_3$); 2.32-2.95 (m, 5H, C=OCHCH$_2$, C=OCHCH$_2$, SC H$_2$CHOH); 3.37-4.42 (m, 16H, PG-backbone, NHCH$_2$CH$_2$, NHCH$_2$CH$_2$, SCH$_2$CHOH, CH$_2$OHCHOH) ppm. $^{13}$C-NMR (176 MHz, CD$_3$OD): δ=17.2 (CH$_3$); 36.7 (SCH$_2$CHCH$_3$); 37.0 (SCH$_2$CHOH); 40.9 (NHCH$_2$); 41.5 (CH$_3$CH); 62.8 (PG-backbone); 64.5 (NHCH$_2$CH$_2$); 65.9 (CH$_2$OHCHOH); 67.2, 69.8, 70.1, 70.6, 70.9, 71.2, 71.4 (PG-backbone); 72.4 (SCH$_2$CHOH); 73.6, 73.9, 79.8, 80.1, 81.4, 81.5 (PG-backbone); 158.5; 158.8 (NHC=O); 176.7 (CHC=O) ppm. IR $v_{max}$: 775 (m), 876 (m), 930 (m), 1035 (s), 1067 (s), 1156 (s), 1251 (s), 1342 (m), 1377 (m), 1411 (m), 1457 (m), 1538 (m), 1704 (s), 2357 (w), 2876 (m), 2923 (m), 3361 (m) cm$^{-1}$.

Dendritic Polyglycerol Thioglyceryl Methylpropanoatyl Sulfate (dPG-TMPS) (5)

dPG-thioglyceryl methylpropanoatyl sulfate was synthesized according to the general procedure for sulfation by applying dPG-thioglyceryl methylpropanoate (14,300 g mol$^{-1}$, 105 OH groups). The compound was obtained as colorless solid after freeze-drying. $M_n$ (dPG-core)=5,100 g$^{-1}$ $M_n$=22,600 g mol$^{-1}$, dF=78%, yield: 84%.

$^1$H-NMR (400 MHz, D$_2$O): δ=1.28 (s, br, 3H, CH$_3$); 2.59-3.09 (m, 5H, C=OCHCH$_2$, C=OCHCH$_2$, SC H$_2$CHOSO$_3$); 3.22-4.74 (m, 16H, PG-backbone, NHC H$_2$CH$_2$, NHCH$_2$CH$_2$, SCH$_2$CHOH, CH$_2$OHCHOH) ppm. $^{13}$C-NMR (176 MHz, D$_2$O): δ=16.2 (CH$_3$); 32.1 (S CH$_2$CHCH$_3$); 35.1, 35.3 (SCH$_2$CHOSO$_3$); 39.4 (NHCH$_2$); 40.1 (CH$_3$CH); 60.5 (PG-backbone); 63.9 (NHCH$_2$CH$_2$); 66.8 (CH$_2$OHCHOH); 67.6, 68.5, 68.5, 70.1 (PG-backbone); 75.9, 76.5 (SCH$_2$CHOSO3); 77.2, 78.2 (PG-backbone); 158.0, 158.6 (NHC=O); 177.6 (CHC=O) ppm. IR $v_{max}$: 774 (m), 810 (w), 922 (m), 998 (s), 1037 (s), 1064 (s), 1102 (s), 1159 (s), 1216 (s), 1346 (w), 1376 (w), 1415 (w), 1457 (m), 1538 (m), 1705 (s), 2881 (w), 2936 (m), 3370 (m) cm$^{-1}$.

Clotting Assay

The clotting assays were performed for activated partial thromboplastin time (APTT) at individual concentrations using an Amelung coagulometer (Type 410A4MD). The measurements refer to the clotting time [s] of the untreated plasma control which was set to 100%. To determine the APTT, 100 µl plasma and 100 µl Actin FS were mixed and incubated (3 min, 37° C.) with 4 µl test compound (final concentrations 0-1000 nM). The reaction was started by the addition of 100 µl of pre-warmed (37° C.) clotting activator CaCl$_2$. The data are presented as mean±S.D. of two independent experiments.

Complement Activation Assay

Normal pooled human serum from six donors was obtained by centrifugation (20 min, 4° C., 3400×g) of coagulated blood samples. The supernatant was stored in 100 µl aliquots at −20° C. until use and then thawed for one minute at 37° C. Complement activation was tested for the classical pathway with an ELISA-based assay. Briefly, a multi-well plate setup with IgM coated wells was used for activation of the classical complement pathway. Therefore, 100 µl of freshly thawed and diluted (1:101) serum samples were incubated (60 min, 37° C.) with 2 µl test compound (final concentrations 0-2500 nM). The formation of the specific complement membrane attack complex (MAC), the membrane pore with components C5b-9 was detected with an alkaline phosphatase (AP)-labeled antibody and substrate para-nitrophenylphosphate (PNPP). Absorbance at 405 nm was recorded with a SpectraMax 340PC. The stated values for any concentration are the mean±S.D. of 2-3 independent measurements.

The biodistribution of embodiments of polyglycerol derivatives according to the claimed invention was tested in comparison to the biodistribution of polyglycerol derivatives according to prior art. By these experiments, it could be shown that the linker being present in the polyglycerol derivatives according to the claimed invention serves for much more favorable biodistribution of the polyglycerol derivatives. Some of these experiments will be explained in the following.

Figure 9:
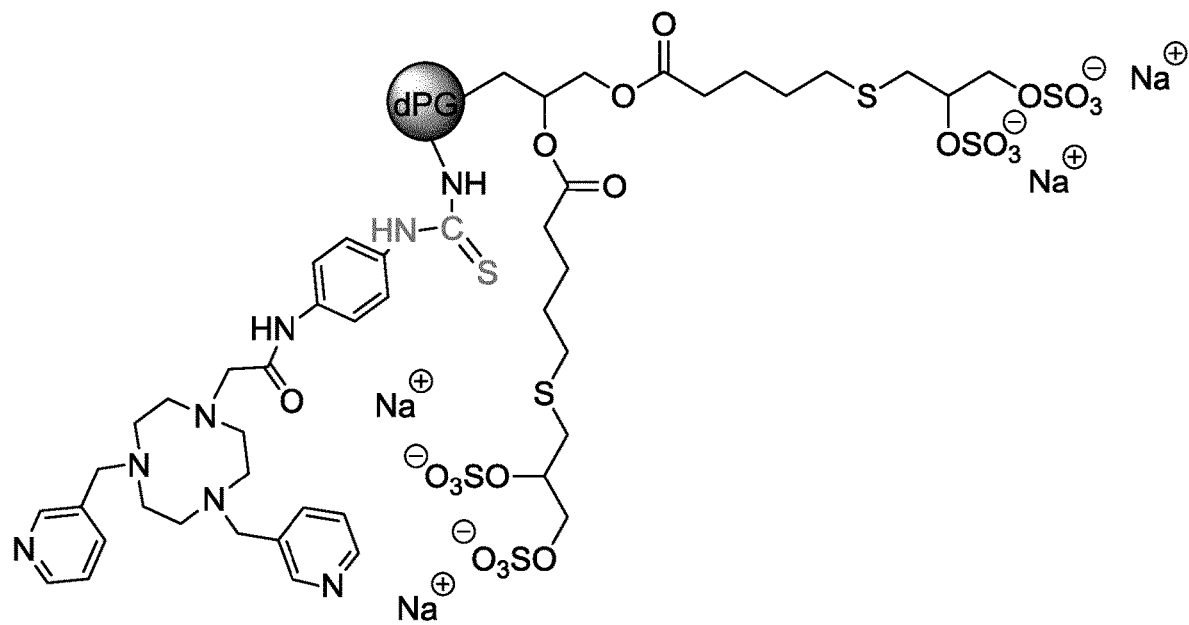
FIG. 9 shows the chemical structure of dPG-DMPTACN-TPS.
Figure 10:
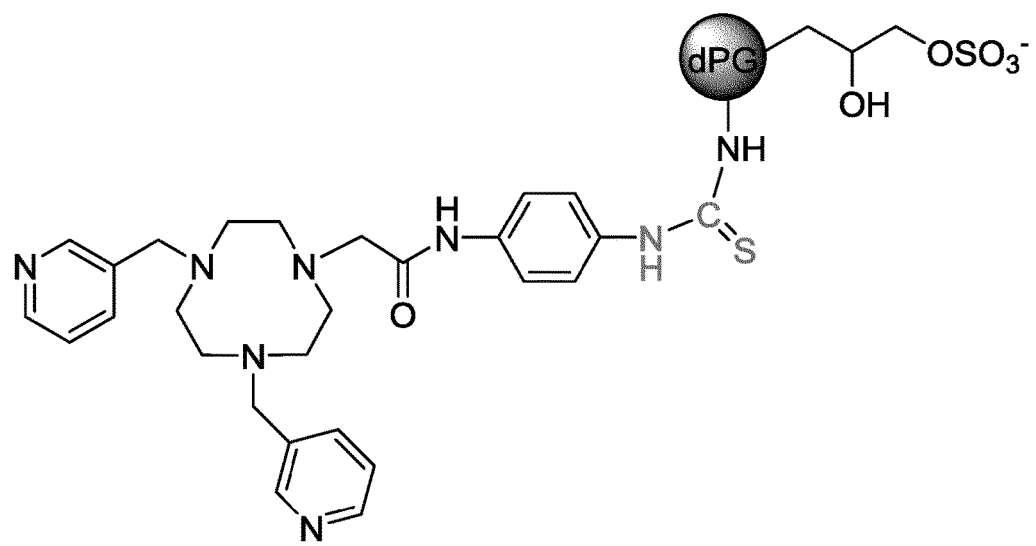
FIG. 10 shows the chemical structure of dPGS-DMP-TACN.

The compound dPG-DMPTACN-TPS was tested as exemplary embodiment in comparison to dPGS-DMPTACN. Both dPG-DMPTACN-TPS and dPGS-DMPTACN comprise a 1,4-bis(2-pyridinylmethyl)-1,4,7-triazacyclononane (DMPTACN) residue. The chemical structure of dPG-DMPTACN-TPS is depicted in FIG. 9, and the chemical structure of dPGS-DMPTACN is shown in FIG. 10. The linker used for dPG-DMPTACN-TPS comprises eight carbon atoms and one disulfide bridge. It is connected to the polyglycerol core by an ester linkage. Two sulfate groups are linked to the linker. In case of dPGS-DMPTACN, the sulfate group is directly coupled to the polyglycerol core.

The biodistribution of dPG-DMPTACN-TPS and dPGS-DMPTACN was tested 4 hours and 24 hours after administration. Thereby, the recovered percentage of the administered dose in different organs and in urine has been determined. The results are summarized in the following Table 2.

TABLE 2

Results of biodistribution experiments.

| Organ | Biodistribution after 4 hours (% of administered dose) | | Biodistribution after 24 hours (% of administered dose) | |
|---|---|---|---|---|
| | dPG-DMPTACN-TPS | dPGS-DMPTACN | dPG-DMPTACN-TPS | dPGS-DMPTACN |
| Spleen | 0.43 | 1.20 | 0.47 | 1.21 |
| Kidney | 4.68 | 4.28 | 1.79 | 3.04 |
| Liver | 3.58 | 5.55 | 1.53 | 3.11 |
| Duodenum | 3.54 | 12.71 | 9.01 | 4.44 |
| Colon | 0.80 | 0.53 | 6.54 | 0.29 |
| Urine | 1.94 | 20.33 | 31.67 | 31.05 | dPG-DMPTACN-TPS accumulates to a significantly lower extent than dPGS-DMPTACN in spleen both after 4 hours and after 24 hours.

In kidney, the accumulation of dPG-DMPTACN-TPS after 4 hours is comparable to the accumulation of dPGS-DMPTACN (considering the standard deviation of the performed experiments). After 24 hours, the accumulation of dPG-DMPTACN-TPS is significantly lower than the accumulation of dPGS-DMPTACN.

In liver, the accumulation of dPG-DMPTACN-TPS is again significantly lower than the accumulation of dPGS-DMPTACN after 4 hours and after 24 hours.

In the duodenum, accumulation of dPG-DMPTACN-TPS is significantly lower than the accumulation of dPGS-DMPTACN after 4 hours, but higher after 24 hours. This indicates that the excretion pathway via the duodenum is taken later in case of dPG-DMPTACN-TPS.

Interestingly, the recovery rate of dPG-DMPTACN-TPS in the colon is comparable to that of dPGS-DMPTACN after 4 hours, but an order of magnitude higher after 24 hours. It appears that—although dPGS-DMPTACN is accumulated in the duodenum—no significant excretion of dPGS-DMPTACN via the colon takes place. Rather, it appears that an absorption in the duodenum of dPGS-DMPTACN might occur. In contrast, the obtained data clearly shows that dPG-DMPTACN-TPS is excreted via the colon after 24 hours.

In urine, a lower occurrence of dPG-DMPTACN-TPS than of dPGS-DMPTACN is observed after 4 hours. However, after 24 hours, the recovery rate of dPG-DMPTACN-TPS equals the recovery rate of dPGS-DMPTACN.

Summarizing, the obtained data clearly shows that dPG-DMPTACN-TPS is less accumulated than dPGS-DMPTACN in spleen, kidney and liver either after 24 hours or after 4 hours and after 24 hours. The data further shows that the excretion of dPG-DMPTACN-TPS via the duodenum and the colon is significantly better than that of dPGS-DMPTACN. In addition, the excretion of dPG-DMPTACN-TPS via urine equals the excretion of dPGS-DMPTACN after 24 hours.

Therewith, the linker being present in dPG-DMPTACN-TPS provides this compound with a favorable biodistribution behavior with respect to dPGS-DMPTACN having no such linker.

LIST OF REFERENCES CITED IN THE PRECEDING SECTIONS

[1] H. Türk, R. Haag, S. Alban, Bioconjugate Chemistry 2004, 15, 162-167.

[2] M. Weinhart, D. Gröger, S. Enders, S. B. Riese, J. Dernedde, R. K. Kainthan, D. E. Brooks, R. Haag, Macromolecular Bioscience 2011, 11, 1088-1098.

[3] M. Weinhart, D. Gröger, S. Enders, J. Dernedde, R. Haag, Biomacromolecules 2011, 12, 2502-2511.

[4] J. Dernedde, A. Rausch, M. Weinhart, S. Enders, R. Tauber, K. Licha, M. Schirner, U. Zügel, A. von Bonin, R. Haag, Proceedings of the National Academy of Sciences 2010, 107, 19679-19684.

[5] K. Oishi, Y. Hamaguchi, T. Matsushita, M. Hasegawa, N. Okiyama, J. Dernedde, M. Weinhart, R. Haag, T. F. Tedder, K. Takehara, H. Kohsaka, M. Fujimoto, Arthritis & Rheumatology 2014, 66, 1864-1871.

[6] K. Licha, P. Welker, M. Weinhart, N. Wegner, S. Kern, S. Reichert, I. Gemeinhardt, C. Weissbach, B. Ebert, R. Haag, M. Schirner, Bioconjugate Chemistry 2011, 22, 2453-2460.

[7] D. Gröger, F. Paulus, K. Licha, P. Welker, M. Weinhart, C. Holzhausen, L. Mundhenk, A. D. Gruber, U. Abram, R. Haag, Bioconjugate Chemistry 2013, 24, 1507-1514.

[8] C. Holzhausen, D. Gröger, L. Mundhenk, P. Welker, R. Haag, A. D. Gruber, Nanomedicine: Nanotechnology, Biology and Medicine 2013, 9, 465-468.

[9] A. Sunder, R. Hanselmann, H. Frey, R. Mülhaupt, Macromolecules 1999, 32, 4240-4246.

[10] G. Pickaert, M. Cesario, R. Ziessel, The Journal of Organic Chemistry 2004, 69, 5335-5341.

[11] S. J. Bryant, K. A. Davis-Arehart, N. Luo, R. K. Shoemaker, J. A. Arthur, K. S. Anseth, Macromolecules 2004, 37, 6726-6733.

[12] S. Enders, G. Bernhard, A. Zakrzewicz, R. Tauber, Biochimica et Biophysica Acta (BBA)—General Subjects 2007, 1770, 1441-1449.

[13] M. Kirschfink, Immunopharmacology 1997, 38, 51-62.

The invention claimed is:

1. A polyglycerol derivative, comprising a dendritic polyglycerol backbone and at least one negatively charged substituent selected from the group consisting of sulfates, sulfonates, phosphates, phosphonates, bisphosphonates, carboxylates, and a combination thereof, wherein the at least one negatively charged substituent is bonded to the polyglycerol backbone via a linker, wherein the linker is selected from the group consisting of a moiety comprising a carbamate group, a moiety comprising an ester group, a moiety comprising an orthoester group, a moiety comprising an amide group, a moiety comprising a disulfide bridge group, a moiety comprising an acetal group, a moiety comprising an imine group, a carbamate group, an ester group, an orthoester group, an amide group, a disulfide bridge group, an acetal group, an imine group, and a combination thereof, wherein the linker comprises 1 to 10 carbon atoms, and wherein a plurality of hydroxyl groups of the polyglycerol backbone is substituted by at least one of the following substituents R, the counter-ion being optionally different from Na+:

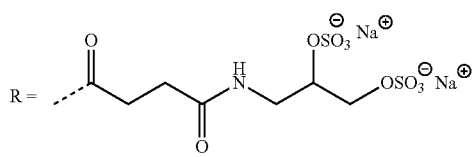

(I)

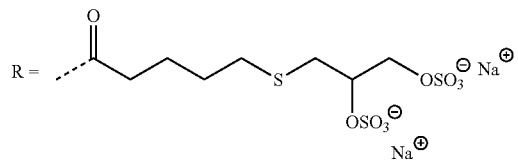

(II)

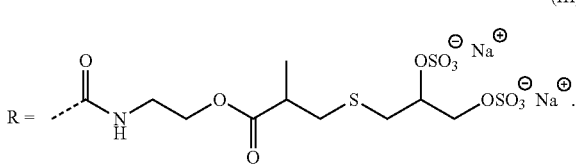

(III)

2. The polyglycerol derivative according to claim 1, wherein the at least one negatively charged substituent is a sulfate.

3. The polyglycerol derivative according to claim 1, wherein the polyglycerol backbone has a degree of substitution between 10 and 100%.

4. The polyglycerol derivative according to claim 1, wherein the linker is an ester group or the linker comprises an ester group.

5. The polyglycerol derivative according to claim 1, wherein the linker is a substituted or non-substituted hydrocarbon residue that is optionally interrupted by at least one N, O and/or S atom and that comprises a carbamate group, an ester group, an orthoester group, an amide group, a disulfide bridge group, an acetal group, an imine group, or a combination thereof.

6. The polyglycerol derivative according to claim 5, wherein the hydrocarbon residue is a substituted or non-substituted $C_1$-$C_{10}$ alkyl that comprises a carbamate group, an ester group, an orthoester group, an amide group, a disulfide bridge group, an acetal group, an imine group, and a combination thereof, and wherein the hydrocarbon residue is optionally interrupted by at least one N, O and/or S atom.

7. A medicament comprising a pharmaceutically active substance and the polyglycerol derivative according to claim 1 as a carrier for the pharmaceutically active substance.

8. A medicament according to claim 7 for inhibiting the complement system of an organism and/or for inhibiting L-selectin binding to its natural receptor.

9. A medicament according to claim 7 for treating an inflammatory disease.

* * * * *